United States Patent [19]

Doi et al.

[11] Patent Number: 4,851,984
[45] Date of Patent: Jul. 25, 1989

[54] METHOD AND SYSTEM FOR LOCALIZATION OF INTER-RIB SPACES AND AUTOMATED LUNG TEXTURE ANALYSIS IN DIGITAL CHEST RADIOGRAPHS

[75] Inventors: Kunio Doi, Willowbrook; Shigehiko Katsuragawa, Clarendon Hills, both of Ill.

[73] Assignee: University of Chicago, Chicago, Ill.

[21] Appl. No.: 81,143

[22] Filed: Aug. 3, 1987

[51] Int. Cl.$^4$ ............................................. G06F 15/42
[52] U.S. Cl. ............................... 364/413.23; 358/111; 378/901; 382/6
[58] Field of Search ..................... 364/414; 378/99, 90, 378/901; 382/54, 52, 6; 358/111

[56] References Cited

U.S. PATENT DOCUMENTS

| | | | |
|---|---|---|---|
| 4,630,202 | 12/1986 | Mori | 364/414 |
| 4,682,291 | 7/1987 | Reuveni | 378/901 |
| 4,707,786 | 11/1987 | Dehner | 382/6 |
| 4,752,879 | 7/1988 | Brunnet | 378/901 |

Primary Examiner—A. D. Pellinen
Assistant Examiner—Jeffrey A. Gaffin
Attorney, Agent, or Firm—Oblon, Spivak, McClelland, Maier & Neustadt

[57] ABSTRACT

A method and system for automated analysis of digital radiographic images in which regions-of-interest (ROI's) are first determined, and subsequently analyzed for abnormalities. To locate the ROI's, the outer ribcage and midline boundary locations of the chest image are determined from the digital image data. Vertical profiles are then selected and background trend is then removed from each vertical profile. A shift-variant sinusoidal function is fitted to each vertical profile and ROI's are selected based on the fitted functions. The non-uniform background trend is removed from the original image data of each selected ROI to obtain corrected data. The power spectrum of the lung texture is obtained from the 2D Fourier transform of the corrected data and is filtered by the human visual response. Finally, the root-mean-square (rms) variation, R, and the first moment of the power spectrum, M, are determined as quantitative texture measures for the magnitude and coarseness (or fineness), respectively, of the lung texture.

62 Claims, 17 Drawing Sheets

METHOD AND SYSTEM FOR LOCALIZATION OF INTER-RIB SPACES AND AUTOMATED LUNG TEXTURE ANALYSIS IN DIGITAL CHEST RADIOGRAPHS

BACKGROUND OF THE INVENTION

1. Field of the Invention

This invention relates to a method and apparatus for automated analysis of digital chest radiographs, and more particularly to automated methods and apparatus for localization of inter-rib spaces for lung texture analysis and detection and characterization of interstitial lung disease in digital chest radiographs.

2. Discussion of Background

A potential advantage of digital radiography is the capability for quantitative analyses of image features representing normal and abnormal patterns, and the subsequent use of these data to aid radiologists' diagnoses. For example, digital image analysis techniques are being developed to detect microcalcifications in mammograms; detect lung nodules in chest radiographs; and track opacified vessels and assess stenotic lesions and blood flow data in angiograms.

The requirements for an automated approach to determine positions of regions of interest (ROIs) for sampling lung textures in a digital chest image are relatively simple. Appropriate ROIs containing lung textures must be free from rib structures, large vessels, and image artifacts. Also, for reasons of practicality, these ROIs must be selected as fast as possible.

There have been many attempts to determine the location of ribs in a chest image. The determination of rib locations is almost equivalent to finding the position of inter-rib spaces which are possibly suitable for sampling lung textures. Wechsler et al., Computer Graphics Image Processing 7, 375-390, 1978, formulated a method to detect posterior and anterior ribs on a chest image by using image processing techniques which included filtering, edge detection, and Hough transforms. An error rate of 10-15% on a small test set of five 256×256 chest images was reported with an average computation time of 18 minutes on a DEC PDP 11/45 computer. Other methods are based on the analyses of vertical profiles taken through the lung fields, and attempt to identify rib edge points which can later be fitted with a curve. However, straight-forward edge detection is not adequate because (1) there are very many edges in a chest image and (2) rib edges are not apparent in some cases, especially where interstitial disease is present.

Using statistical tests, DeSousa, Computer Vision, Graphics, and Image Processing 23, 1-14, 129-161, (1983) has presented an automatic rib detection method that works by locating the ribs on a small number of vertical profiles through the lung fields in 400×400 posterior/anterior chest images. Using this approach, DeSouza reported satisfactory results but gave no indication of the number of cases used in his investigations. Although some of these approaches to the determination of rib locations may be applicable to locate inter-rib spaces for lung texture analysis, these methods require more computations than are typically necessary.

An automated technique for identification of ROI's would be particularly useful in connection with an automated technique for detection and analysis of interstitial lung disease.

Interstitial lung disease is a common clinical entity. Chest radiography constitutes about 40% of hospital-based X-ray examinations in the United states. Approximately 22% of lung abnormalities seen in chest radiographs at the University of Chicago Medical Center are due to interstitial abnormalities. Interstitial disease is defined as an abnormality of the interstitial compartments of the lung, which may be due to infiltration by inflammatory or neoplastic cells or may be a consequence of the accumulation of fluid or proteinaceous material.

It is recognized that evaluation of diffuse interstitial disease in chest radiographs is one of the most difficult problems in diagnostic radiology. This difficulty is due to (1) the numerous patterns and complex variations that are involved, (2) the lack of firmly established correlation between radiologic and pathologic findings, and (3) variations among radiologists in the terms that they use to describe radiographic patterns, which are not defined objectively. The great proliferation of descriptive adjectives used produces considerable variations in interpretation among individuals, institutions, textbooks, and even by the same individual on different days.

If quantitative computerized methods can be developed which provide objective assessment of lung texture patterns, then this subjectivity could be reduced and the accuracy in radiologic interpretation increased. Investigators have been searching for many years for an automated means of detecting and quantifying the severity of coal workers' pneumoconiosis as well as other forms of pulmonary infiltrates. In order to differentiate a normal lung from a lung with pulmonary fibrosis, Sutton et al, IEEE Trans. Comput. C-21, 667 (1972) devised measures based on the statistical properties of the density distribution on a radiograph. They also measured the frequency content of the Fourier spectrum of the lung texture over a mid-frequency range. Kruger et al., IEEE Trans. Systems, Man and Cybermatics SMC-4:40 (1974) attempted to classify coal workers' pneumoconiosis by using two methods; one of which was a statistical approach in which they used 60 texture measures based on point-to-point variations in reduced gray levels, and the other of which was based on an analysis of the optical Fourier spectrum. Tully et al., Invest. Radiol. 13:298 (1978), used the same statistical method to classify normal lungs, alveolar infiltrates and interstitial infiltrates. Revesz et al., Invest. Radiol. 8:345 (1973), obtained the power spectrum of the lung texture by using the optical Fourier transform in order to distinguish between normal lungs and lungs with interstitial disease. Jagoe et al., British J. Indust. Med 32:267 (1975) and Computer and Biomedical Research 12:1 (1979) employed a method of coding the texture patterns in terms of the directions of the gray-level gradient vector, which was determined by sampling of the chest radiograph at 1.2 mm interval, to investigate the severity of pneumoconiosis.

In the statistical approach, because texture measures were obtained from the pixel values, which were reduced to 8 or 16 gray levels, subtle density variations in a radiograph would have been lost in the case of low-contrast patterns caused by interstitial lung disease. Another problem in previous studies was that texture measures were determined in terms of the density variations, which included the overall lung structure (low-frequency background trend) in the chest radiograph. Thus, previous texture measures were very insensitive to small changes in the fluctuating patterns of the underlying lung texture. Furthermore, investigators failed to demonstrate whether these texture measures corresponded to any features that radiologists normally see in a chest image. Because of these problems, previous attempts to use computer analysis of lung texture for the diagnosis of interstitial disease have not been widely accepted.

SUMMARY OF THE INVENTION

Accordingly, one object of this invention is to provide a novel method and system which efficiently and quickly determines the location of inter-rib spaces for quantitative analysis of lung textures in chest images. Another object of this invention is to provide a novel method and system for automated detection and analysis of interstitial lung disease which overcomes the problems in the reported efforts of other investigators as above discussed.

These and other objects are achieved according to the present invention by providing a new and improved method and system for location of ROI's in a digital chest image wherein the data of the digital chest image is sampled and converted to a smaller array, e.g., $128 \times 128$ pixels; the outer ribcage boundaries are determined; two vertical profiles are selected in each lung, each selected profile is fitted with a shift-variant sinusoidal pattern after non-uniform background trend is removed from each vertical profile; and the location of appropriate ROI's for sampling lung texture is determined. The initial conversion to a smaller array is useful to reduce computation time. Subsequent procedures are performed on the smaller converted array, but can be applied to large arrays.

Further, according to the invention, the fine details of lung texture, which are affected by interstitial disease are isolated, from the gross lung anatomy in determined ROI's of the original digital chest radiographs. In order to detect and characterize interstitial lung disease, objective texture measures based on the power spectrum of the underlying lung texture are derived.

More particularly, in the method and system for automated texture analysis of digital chest radiographs according to the invention, first, a conventional chest radiograph is digitized, and approximately twenty square regions of interest (ROI) are selected from the inter-costal (inter-rib) spaces. The non-uniform background trend in each ROI is corrected by means of a two-dimensional (2D) surface fitting technique in order to determine the fluctuating patterns of the underlying lung texture for subsequent computer analysis. The power spectrum of the lung texture is obtained from the 2D Fourier transform and is filtered by the visual system response of the human observer. Finally, the root-mean-square (rms) variation, R, and the first moment of the power spectrum, M, are determined as quantitative texture measures for the magnitude and coarseness (or fineness), respectively, of the lung texture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
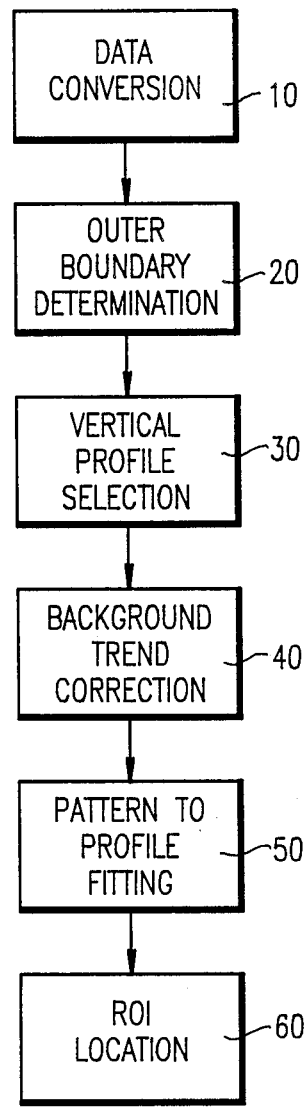
FIGS. 1a and 1b are schematic block diagrams illustrating the ROI location method of the invention.

Referring now to the drawings, wherein like reference numerals designate identical or corresponding parts throughout the several views, and more particularly to FIG. 1a thereof, the method to locate ROIs in a digital chest image includes the following steps: conversion of the digital chest image to a $128 \times 128$ array by sampling the data in the original chest image (block 10); (2) determination of the outer ribcage boundaries (block 20); (3) selection of two vertical profiles in each lung (block 30); (4) background trend correction (block 40); (5) fitting of each profile with a shift-variant sinusoidal pattern (block 50); and (6) determination of the location of appropriate ROIs for sampling lung texture (block 50).

Figure 1B:
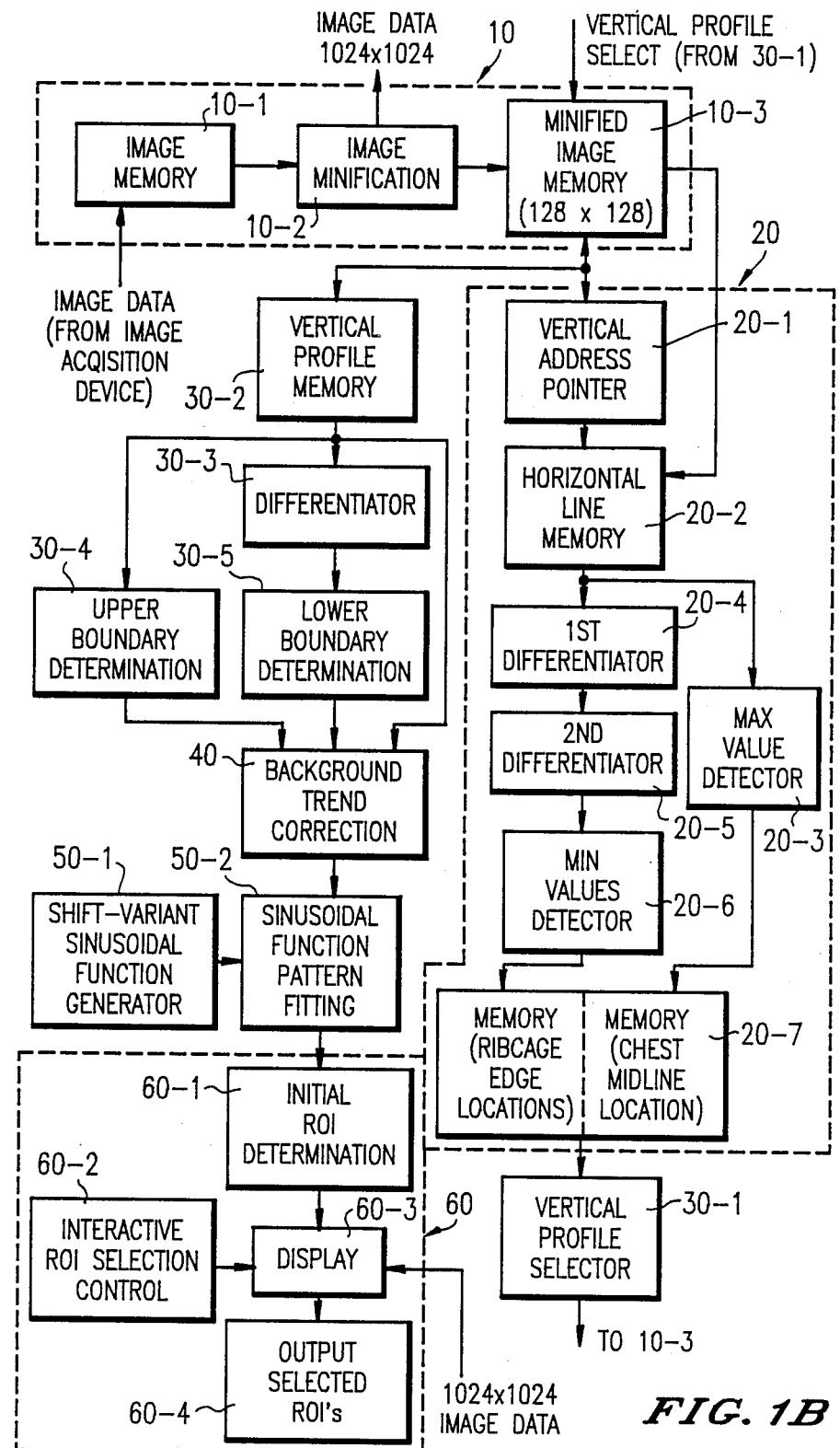

FIG. 1b shows the ROI method location of the invention in more detail, and is discussed hereinafter.

Image Conversion (Minification)

The initial conversion of the digital chest image to a small array is useful to reduce computation time. Image conversion is performed by sampling the image data stored in image memory (10-1) to perform image minification (10-2). Pixel averaging can also be performed. The converted image is then stored in memory (10-3). The subsequent procedures are performed on the 128×128 array but can be applied to large arrays.

Determination of ribcage boundaries

To define the location of ROIs in the lung, it is necessary to identify the approximate area of the lung field in the image. This is achieved by determining locations of ribcage edges on both sides of the chest.

Figure 2A:
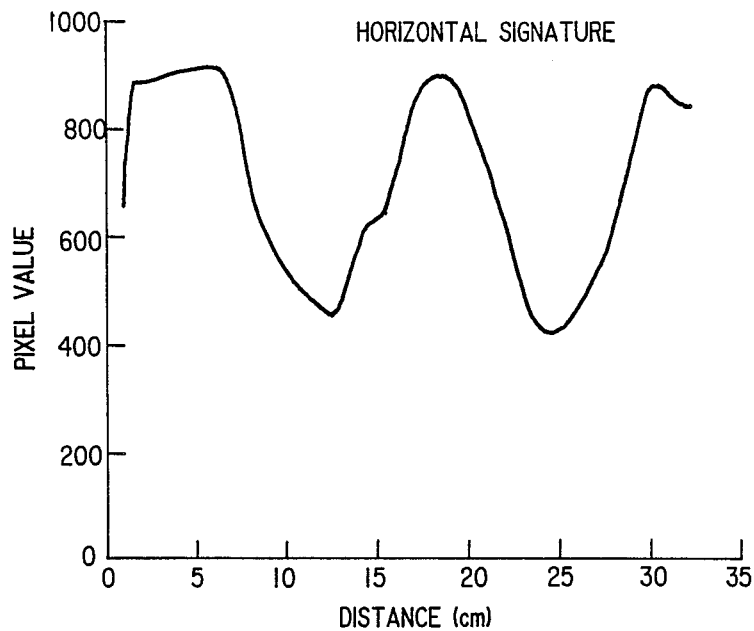
FIGS. 2a and 2b are graphs illustrating a horizontal signature and its second derivative of a ⅛ horizontal section of a chest image.

First, an average horizontal (i.e., generally perpendicular to the spinal column) signature, as shown in FIG. 2(a), across a one-eighth section near the middle of the image is obtained under control of the vertical address pointer (20-1) and stored in memory (20-2). The horizontal "midline" of the chest is determined by locating the highest pixel value near the center of the signature (block 20-3). A first derivative (block 20-4) and a second derivative (block 20-5) of the horizontal signature are obtained. The locations of the initial ribcage boundaries in both lungs are then determined as the positions yielding the minimum values of second derivatives on each side of the midline (block 20-6), and is illustrated in FIG. 2-(b). It is noted that edge detection using first derivatives was found to be not sufficiently sensitive to identify accurate locations of the ribcage edges.

Because only rough estimates of the ribcage edges below the clavicle and above the diaphragm are required for ROI location, upper and lower cutoff levels for the chest image are determined empirically by thresholding the pixel values, and are used to limit the number of additional ribcage edge positions determined.

Figure 2B:
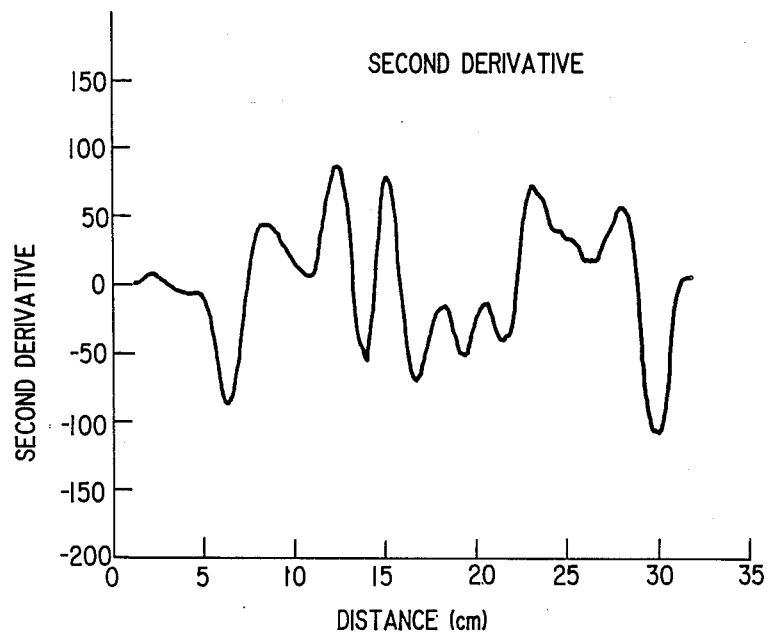

Locations of additional ribcage edges are estimated from the second derivatives curve shown in FIG. 2b along short segments of horizontal lines which are sampled over the approximate location of the ribcage boundaries (block 20-6). The horizontal positions of previously determined ribcage edges are used as a guide to determine the horizontal range for a potential ribcage location. For the determination of approximate locations of ribcage edges, it is adequate to use every eighth line (in the 128×128 array image) above and below the location of the initially determined ribcage edges, with the last upper horizontal segment located just above the upper cutoff level and the lowest segment sampled being slightly below the lower cutoff level. Therefore, for a typical chest image, 7-14 ribcage edge positions are determined for each ribcage edge. The coordinates for these ribcage edges are then fitted with third order polynomials. This fitting technique was applied to 66 chest images from which it was determined that it provides adequate smoothing of ribcage edges to provide ribcage boundaries.

Selection of vertical profiles in the peripheral lung

Due to the presence of vascular, cardiac, and other prominent structures in the central portion of chest images, interstitial disease is more evident in the peripheral regions of the lungs. For this reason, vertical profiles located at 5/6ths and 4/6ths of the distance from the midline of the chest to the corresponding fitted smooth curves defining the ribcage boundaries are selected (block 30-1) and stored in profile memory (block 30-2). The length of each profile is limited by a common upper boundary (i.e., the top cutoff level) arbitrarily selected from one of the vertical profiles (block 30-4) and a lower boundary corresponding to the diaphragm edge. This lower boundary of each profile is estimated (block 30-5) for each vertical profile by locating a maximum value in the first derivative (block 30-3) of the respective profile data near the lower portion of the image.

Fitting of the vertical profile data

Vertical profiles of a chest image include a combination of low pixel values for lungs and high pixel values for the posterior ribs. Also, the vertical profiles reveal that the distance between the ribs tends to increase towards the bottom of the lungs. Therefore, a shift-variant sinusoidal function is generated (block 50-1) and employed as a mathematical model to approximate "global" features of vertical profiles in chest images. Instead of attempting to locate rib edges directly in a vertical profile, according to the invention, locations of inter-rib spaces are estimated using a shift-variant sinusoidal fit of the vertical profile data (block 50-2). Since this approach is based on the overall data set rather than local features such as individual edges, the result is expected to be relatively unaffected when the rib edges may not be well defined due to the low contrast of ribs or when there are a small number of local irregular patterns such as a surgical clip.

Correction for background trend

Figure 3:
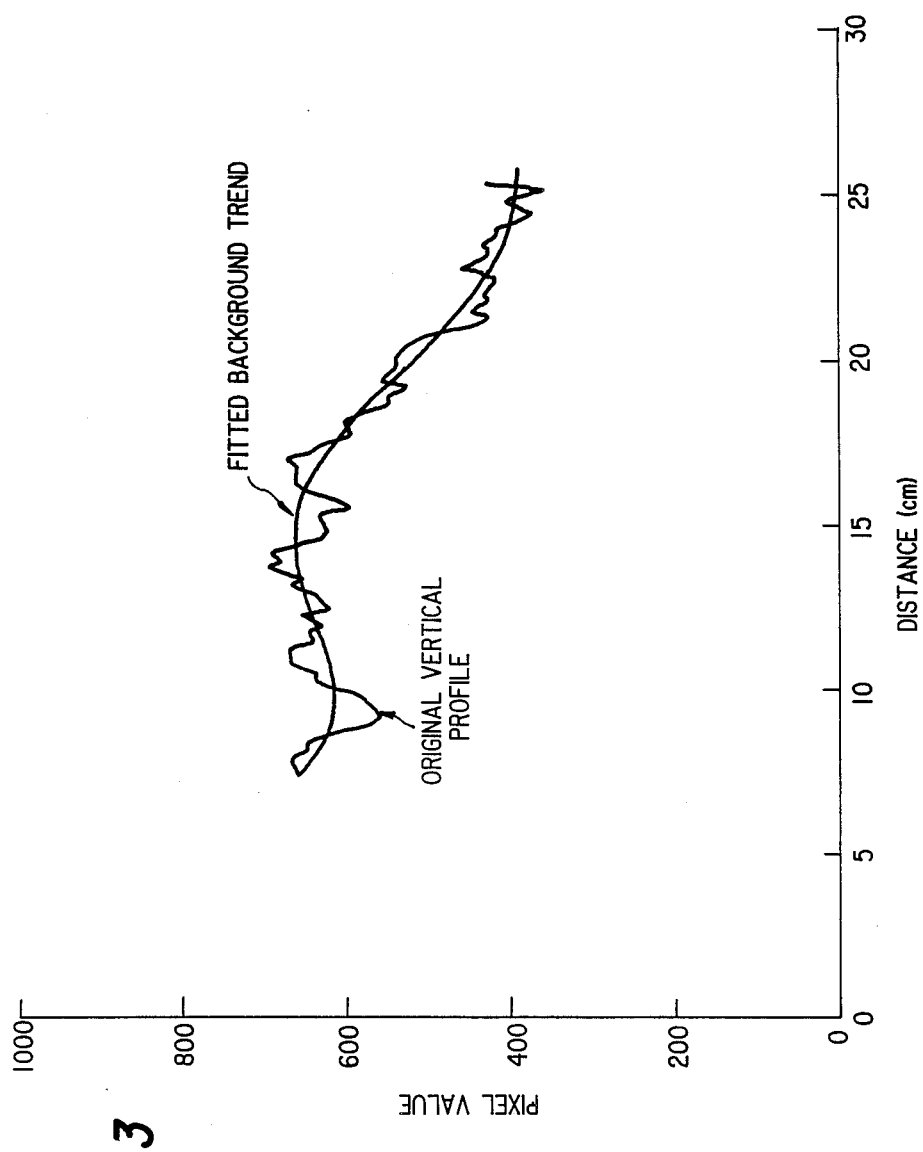
FIG. 3 is a graph illustrating original vertical profile data and a shift-variant sinusoidal function fitted to the vertical profile data.

Although the sinusoidal (or cyclic) nature of the ribs and inter-rib spaces is apparent, the actual vertical profile data do not clearly exhibit this pattern due to underlying background variations in chest images. Therefore, vertical profile data are corrected for the local background trend (block 40). The non-uniform background included in a vertical profile is estimated by fitting the original data with a polynomial curve. After testing 2nd–6th order polynomials, it was determined that 6th order polynomial curves provided the best fit of background trends as illustrated in FIG. 3. Background corrected profile data are obtained by subtracting the fitted background trend from the original profile data.

Shift-variant sinusoidal function for fitting vertical profiles

A shift-variant sinusoidal function is generated in block 50-1 and is given by $$F(x) = A \cos(2\pi u(x)x + \phi) \qquad (1)$$

where $F(x)$ corresponds to the background corrected profile, $u(x)$ is the spatial frequency at a position x, A is the amplitude of the profile, and $\phi$ is a phase term. The spatial frequency may be written as $$u(x) = \frac{1.0}{1(x)} \quad (2)$$

where l(x) is the rib plus inter-rib distance at x. Here, the reference position for x=0 is defined as the location of a peak near the center of the profile data.

As a first order approximation, it is assumed that the rib plus inter-rib distance changes linearly with the position of the vertical profile in a PA chest image. Thus, $$l(x) = mx + b \quad (3)$$

where m indicates the rate of change in the rib plus inter-rib distance and b is the "average" rib plus inter-rib distance. Therefore, the parameter b may be written by $$b = \frac{1.0}{u_o} \quad (4)$$

where $u_o$ corresponds to the average spatial frequency of the background corrected vertical profile data, and is determined from the Fourier spectrum of the profile data, as is discussed later.

From these assumptions it follows that the minimum rib plus inter-rib distance, $l_{min}$ (in the upper portion of the lungs) is given by $$l_{min} = mx_{min} + b, \quad (5)$$

and the maximum rib plus inter-rib distance, $l_{max}$ (in the lower portion of the lungs) is given by $$l_{max} = mx_{max} + b, \quad (6)$$

where $x_{min}$ and $x_{max}$ correspond to the upper and lower boundaries of the profile, respectively. It is useful to determine the rate of a change in the rib plus inter-rib space as a function of distance by using the parameter $$k = l_{max}/l_{min}, \quad (7)$$

to indicate the range of rib plus inter-rib distances calculated for a vertical profile. Using this ratio and Eqs. (2)–(7), it follows that $$m = (1-k)/(u_o[kx_{min} - x_{max}]). \quad (8)$$

Using Eqs. (2)–(4) and (8), the spatial frequency is given by $$u(x) = u_o/[\{(1-k)/(kx_{min} - x_{max})\} + 1] \quad (9)$$

Determination of average spatial frequencies

Figure 4:
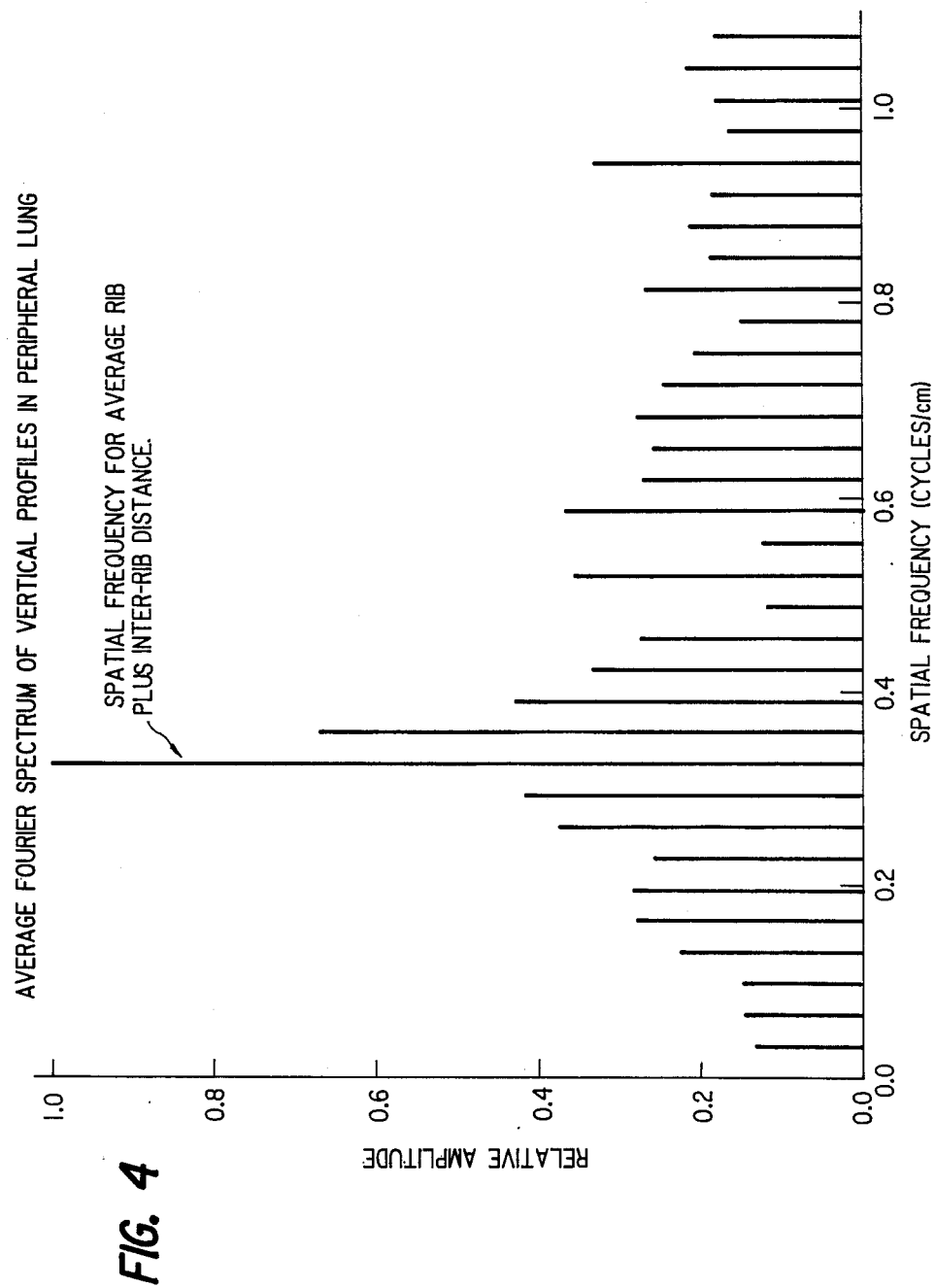
FIG. 4 is a graph illustrating a Fourier transform of background trend corrected vertical profile data.

The spatial frequency for the average rib plus inter-rib distance is determined from the frequency exhibiting the largest amplitude in the Fourier transform of the background corrected profile data for each side of the chest as illustrated in FIG. 4. Since the average spatial frequencies for two vertical profiles selected in each lung are expected to be very similar, the Fourier transforms for the two profiles are averaged. Ideally, the average rib plus inter-rib distance is the same for both lung fields. However, $u_o$ values for each side are determined independently because in many cases patients either cannot be positioned or are not positioned to obtain an image where the rib locations and lung fields for each side of the chest are symmetrical.

Fitting the profile data

Figure 5:
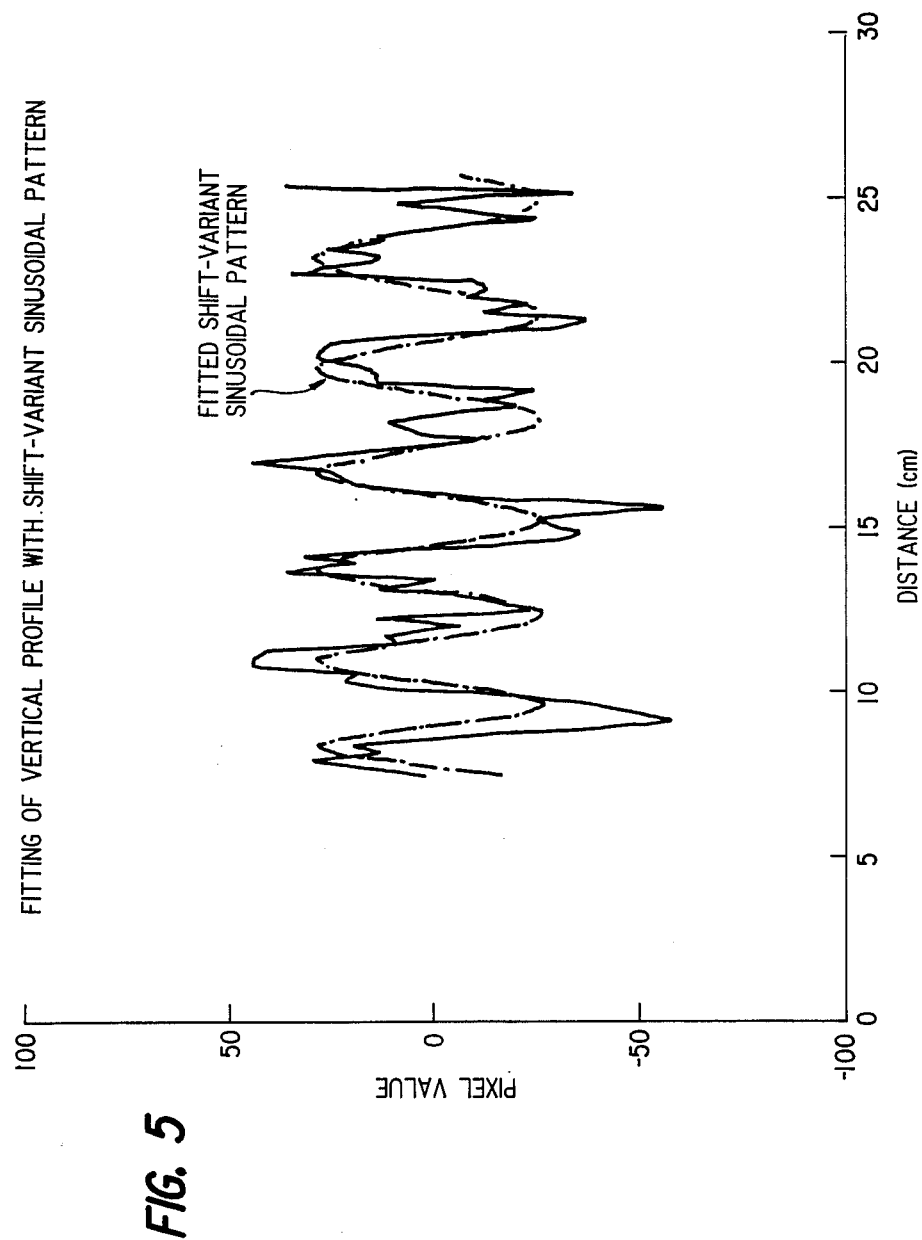
FIG. 5 is a graph illustrating background trend corrected vertical profile data and a shift-variant sinusoidal function fitted thereto.

The next step is to fit the background corrected profile data with a shift-variant sinusoidal curve using the least squares method. The amplitude A of the function F(x) in Eq. (1) is estimated using the root mean square (rms) value of the background corrected profile. For the fitting, the k parameter is changed from 1.2 to 1.8 in increments of 0.1, and $\phi$ is varied from $-0.3\pi$ to $0.3\pi$, in steps of $0.1\pi$. Using these increments it is possible to observe small variations in the calculated rms differences between the profile data and the fitted curves as the two parameters are changed. If a smallest rms difference occurs when $\phi$ equals $-0.3\pi$ or $0.3\pi$, then the value of $\phi$ is further decreased or increased, respectively, until a definite minimum in the rms difference is determined. FIG. 5 shows the comparison of a background corrected profile with a fitted shift-variant sinusoidal curve. It is apparent that approximate locations for the peaks and valleys of the profile correspond well to those of the fitted curve.

From the condition that provides the minimum value in Eq. (1), the locations of inter-rib spaces in a fitted profile are given by $$x = (1/u_0)(n\pi - \phi)/[2\pi - m(n\pi - \phi)] \quad (10)$$

where $n = \pm 1, \pm 3, \pm 5, \ldots$. The practical range of n values is limited by the length of each profile, and the slope m is derived using $u_o$, k, $x_{min}$, and $x_{max}$ (see Eq. (8)).

The above method was used to locate ROIs in inter-rib spaces for 66 chest images that were previously used for observer performance studies on detection of subtle lung abnormalities including nodules, pneumothoraces, interstitial infiltrates, and bone lesions. The size of these ROIs were centrally located at positions given by Eq. (10). The number of these ROIs per image was limited to 22 (6 for the outer profiles and 5 for the inner profiles), which was considered adequate for analysis of lung textures. Rib plus inter-rib lengths were calculated using Eq. (3) in an attempt to avoid the placement of ROIs in small inter-rib spaces which could result in a partial overlap of a ROI with ribs. The results of the automated selection of ROIs for two chest images indicated that all of the ROIs were properly placed in inter-rib spaces. The average time required for the placement of all the ROIs in an image was approximately 4–5 seconds using a DEC VAX 11/750 computer and FORTRAN programming.

For an initial analysis of the performance of the method of the invention, any ROI located between the posterior ribs, regardless of the presence of anterior ribs or vessels, was counted as a successful placement. Any ROIs which overlapped with any part of posterior ribs were regarded as failures unless such an overlap was caused by the small separation between ribs. Using this criterion, 176/280 (63%) of the ROIs located on outer profiles of right lungs (OPRL's); 230/311 (74%) located on inner profiles of right lungs (IPRL's); 203/286 (71%) located on outer profiles of left lungs (OPLL's); and 218/287 (76%) of the ROIs on inner profiles of left lungs (IPLL's) were successfully located in the 66 cases. Thus, the overall success rate was 71% (827/1164).

Figure 6:
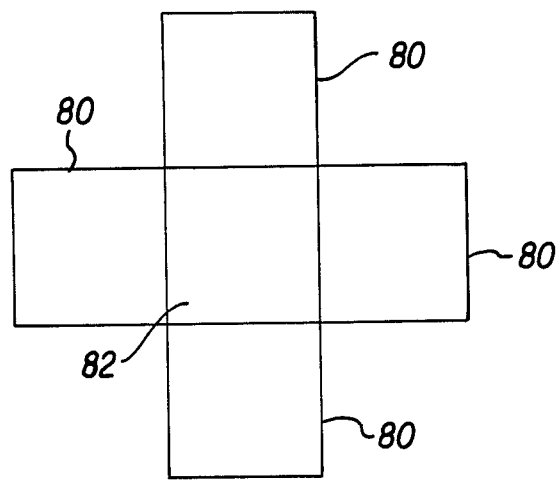
FIG. 6 is an illustrating of plural ROI's located according to the method and system of the invention.

To increase the likelihood of locating appropriate ROIs for sampling lung textures, four additional ROIs 80 are placed around initially determined ROI positions 82, as shown in FIG. 6, to serve as alternative ROIs. Using these additional ROIs and the criterion that a placement is successful if at least one of the five ROIs is located in an inter-rib space, the success rate increases to 269/280 (96%) for OPRL's; 291/311 (94%) for IPRL's; 268/286 (94%) for OPLL's; and 266/287 (93%) for IPLL's; thus yielding an overall success rate of 94% (1094/1164).

Although the above discussed success rate for computerized localization of inter-rib spaces appears to be good, it is still less desirable to employ it for daily use on a large number of clinical studies. This is because if all ROIs are conservatively assumed to be located independently with a success rate of 94%, the overall success rate of locating 18 ROIs in a chest image is expected to be only 33% ($-0.94^{18}$). This implies that a completely automated procedure will require an extremely high rate of correct localization of individual ROI. In order to improve the correct localization rate further, it is useful to analyze the causes for leading to incorrect localizations in the study performed. Errors in mislocation using the above method were primarily due to improper selection of the fundamental frequency $u_o$, incorrect fitting resulting from the presence of prominent anterior ribs, and poor cutoff levels for the bottom of the profiles. Selection of $u_o$ could be improved by using more profiles in each lung. Other methods for estimating lower cutoff levels for the profiles are also being developed. In a few cases, a modification of the assumptions used in the fitting may be necessary to compensate for irregularities in rib structures and the presence of high contrast anterior ribs.

In light of the above discussion, a semi-automated method to locate ROIs for lung texture analyses is also appropriate. With this approach, initial ROI locations are determined (block 60-1) as described and then displayed (block 60-3) at corresponding positions on the image (see FIG. 1b). Using interactive ROI selection control (block 60-2), such as cursor control, an operator then manually revises or deletes some of these initially determined ROIs. After this step, the operator also has the opportunity to select additional ROIs if desired and then output all ROI's identified (block 60-4). This method has been found to be practical and preferable to a totally manual method because it greatly decreases user interaction and still maintains a systematic largely automated procedure. Also, it is beneficial for the user to examine the ROI locations so that obvious mislocations can be quickly identified.

One of the important features of ROI localization according to the present invention is correcting profile data for the non-uniform background trend in block 60, FIG. 1b. It is clear that rib structures in the profile data become more prominent with this correction. Therefore, for chest images with high contrast between ribs and lungs, it may be possible to simply use the background corrected data to locate ROIs at positions where corrected pixel values are less than zero (i.e., locations corresponding to inter-rib spaces). However, for chest images exhibiting areas of low contrast, the fitting with the shift-variant sinusoidal pattern may provide improved results because an entire vertical profile is used to estimate the locations of inter-rib spaces. Clearly, for general applications, a combination of these methods may prove useful.

The ROI's located as described above are then subjected to automated lung texture analysis techniques according to the invention. Before discussing these techniques in detail, the following is a brief description of various considerations in the digitization of chest radiographs.

Digitization of Chest Radiographs

Conventional posterior-anterior (PA) chest radiographs are digitized with a 0.1 mm pixel size and 10-bit analog-to-digital conversion using a Fuji digital image simulation/processing system. In previous studies on observer performance for the detection of interstitial lung disease, it was confirmed that the 0.1 mm pixel size is sufficiently small so that mild interstitial disease can be diagnosed in chest radiographs. The system calibration curve, which indicates the relationship between the pixel value and the optical density, has been carefully maintained so that the optical density range from 0.4 to 2.2 on a film is related linearly to the pixel values in the range of 800 to 200 (i.e., 0.003 optical density/pixel value). The gradient of the curve decreases gradually outside this optical density. Digital chest radiographs are analyzed by an image analysis/processing system, which includes a DEC VAX 11/750 host computer interfaced with a Ramtek 9460 dual-user image processor that has two high-resolution (1280×1024) CRT monitors. The image memory of each processor can store 10-bit image data which are displayed through a 256-gray-level look-up table. Although digitized chest radiographs have been used to perform the lung texture analysis, other types of digital image data from digital radiographic systems, such as the Fuji computed radiography system using storage phosphor-laser readout system and large-format image intensifier—TV digital system can be used for this purpose.

Background Trend Correction

In general, the average optical density of the perihilar area in a chest radiograph is greater than that of the peripheral regions because of differences in the amount of tissue traversed by the x-ray beam in the two locations. The optical densities may commonly differ between these regions by as much as 0.8, which corresponds to about 300 pixel values. Therefore, the variation in optical density observed in the lung field consists of both that due to the gross anatomy of the lung and chest wall (background trend) and that due to the fine underlying texture which is related to interstitial disease. Thus, it is important to isolate underlying density fluctuations from the actual overall lung texture. This pre-processing of lung images, which was also performed in one-dimension on vertical profiles during localization of ROIs, is essential to derive sensitive measures of physical texture for the detection and characterization of interstitial lung disease. It is noted however that while it is adequate to perform background trend correction during ROI location on the converted 128×128 image data matrix, for lung texture analysis, the two dimensional background trend correction is performed on the original image data, typically 4096×4096 pixels.

The background trend in a selected ROI is estimated by using a two-dimensional surface-fitting technique based on the least-square method. Since a high-order polynomial surface tends to fit even relatively small fluctuating patterns due to interstitial diseases and since it requires more computational time, only first- to third-order polynomial surfaces were first examined. It was determined that a second-order polynomial surface provided the largest difference in rms variations between normal and abnormal lungs; therefore, a second-order polynomial surface is selected for background trend correction.

Figure 7C:
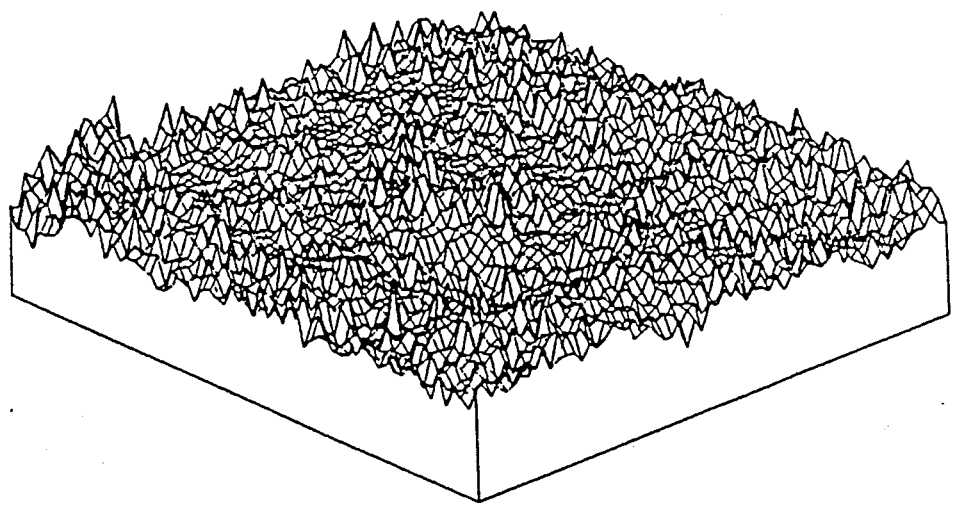
FIGS. 7a, 7b and 7c are perspective illustrations a 2D profile of lung texture image data in a selected ROI, background trend in the selected ROI, and a 2D profile of trend-corrected image data in the selected ROI, respectively.
Figure 7A:
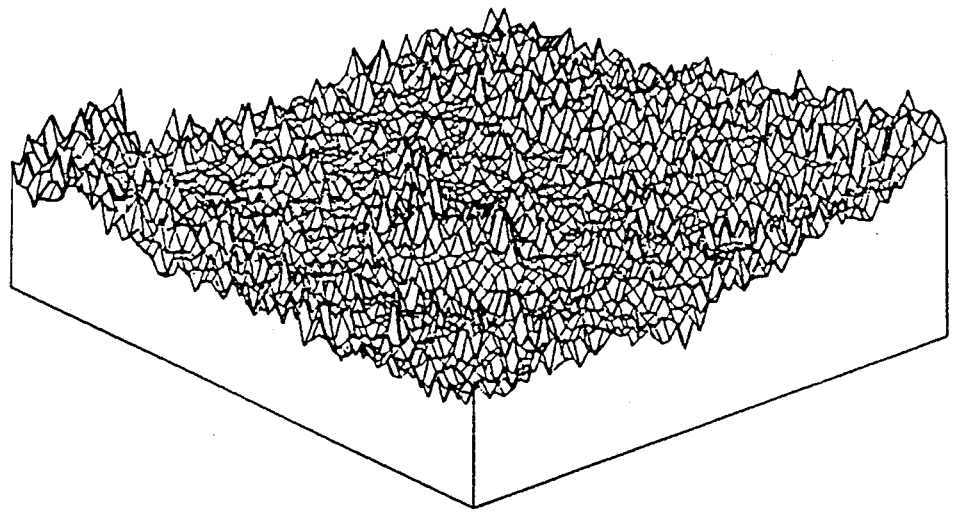
Figure 7B:
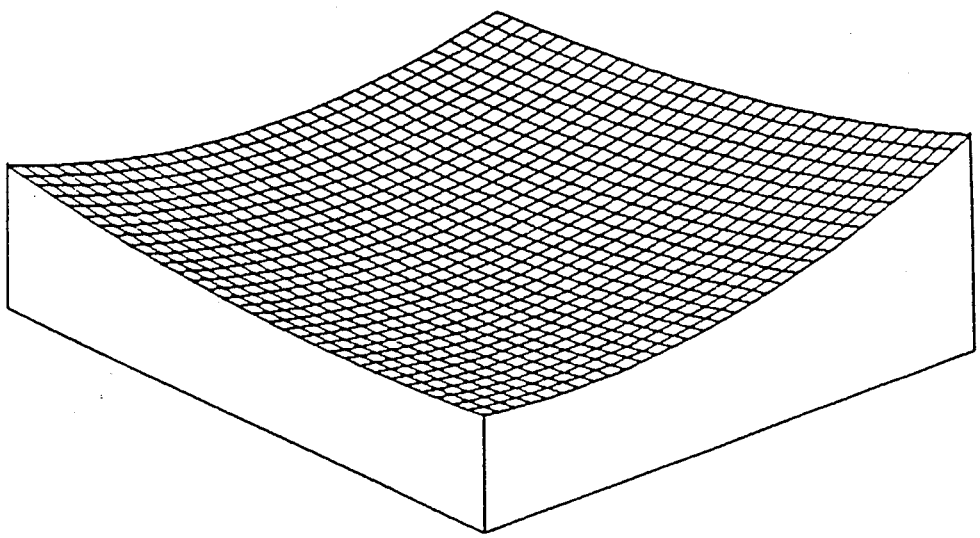

The effect of the background trend correction on two-dimensional profiles of lung texture is demonstrated in FIGS. 7a and 7b. The original image shown in FIG. 7a is selected from the lower left portion of the abnormal lung, and it includes a large amount of background trend that is superimposed on a fluctuating pattern which represents the lung texture. Without the trend correction, the rms variation in this image is 26.6 pixel values. The non-uniform background trend estimated with the two-dimensional surface-fitting technique is shown in FIG. 7b. The trend-corrected image (FIG. 7c) was obtained by subtraction of the background trend (FIG. 7b) from the original image (FIG. 7a). After the trend correction, the overall background appears to be quite uniform. With this correction, the rms variation is reduced to 14.4 pixel values. This result clearly indicates that the background trend strongly affects the rms variation, and that the rms variation of the underlying fluctuating pattern due to the lung texture can differ significantly from that of the fluctuating pattern seen in the original, uncorrected chest image.

Figure 8:
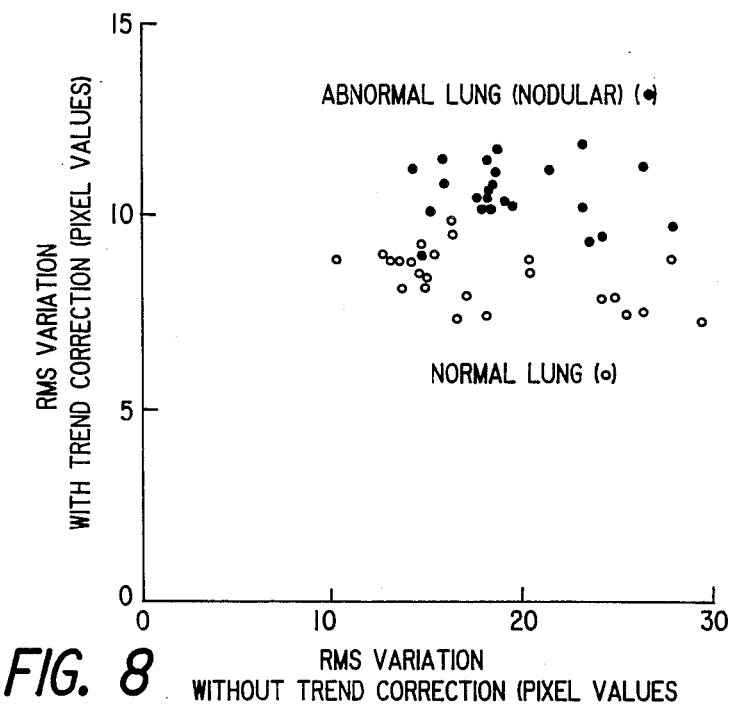
FIG. 8 is a graph illustrating the effect of background trend correction on rms variations for normal and abnormal lungs.

As a demonstration of the usefulness of the background trend correction in distinguishing between normal and abnormal lungs with a nodular pattern, the rms variation of lung textures in various ROIs with and without background trend correction is shown in FIG. 8. From FIG. 8, it is obvious that, without the trend correction, the rms variations of the abnormal lung extensively overlap those of the normal lung, thus making it impossible to distinguish between them. When the background trend is corrected for, the distribution shown in the vertical direction is obtained; now, the rms variations in the abnormal lung are much greater than those in the normal lung. Therefore, for the reliable detection of interstitial disease, it seems necessary to isolate the fine texture from the overall variations in lung density.

Figure 9A:
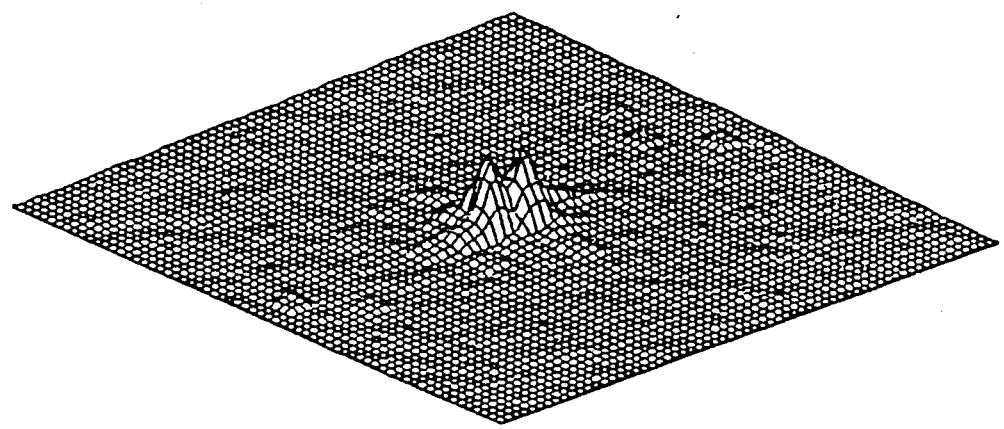
FIGS. 9a, 9b, 9c, and 9d are perspective illustrations of the power spectra of (a) normal lung and (b) abnormal lung, and also power spectra of (c) normal lung and (d) abnormal lung, respectively, filtered by the visual system response of the human observer, wherein the magnitude of power spectra in FIGS. 9(c) and 9(d) is enlarged to eight times as large as that in FIGS. (a) and (9b)
Figure 9B:
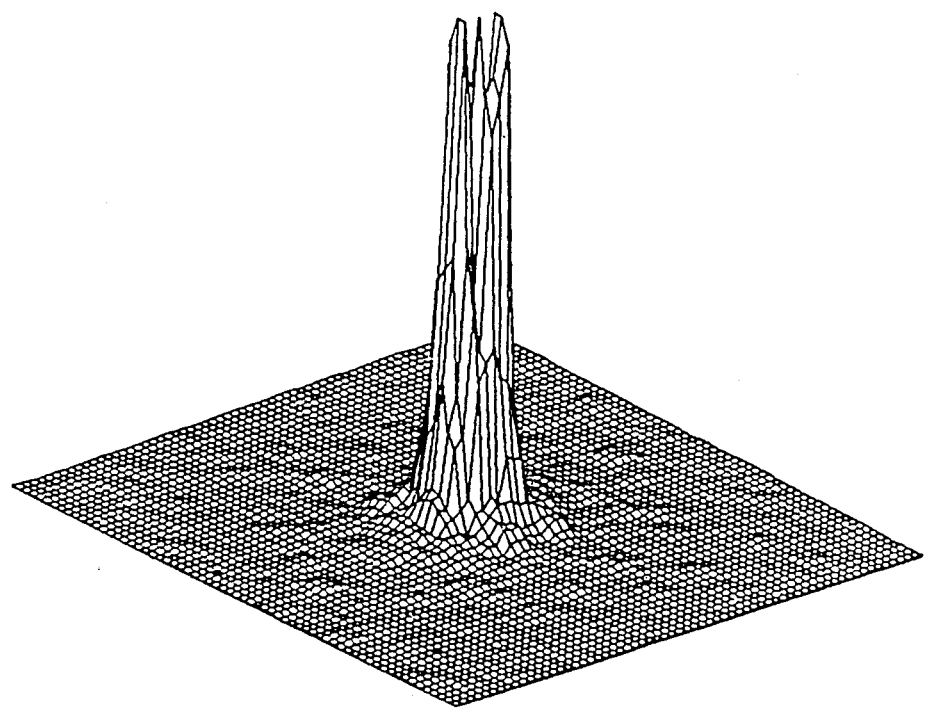
Figure 9C:
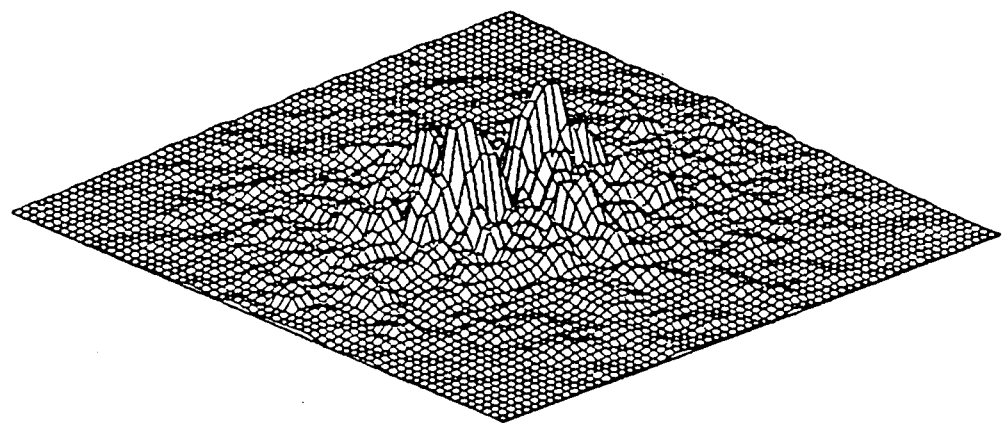
Figure 9D:
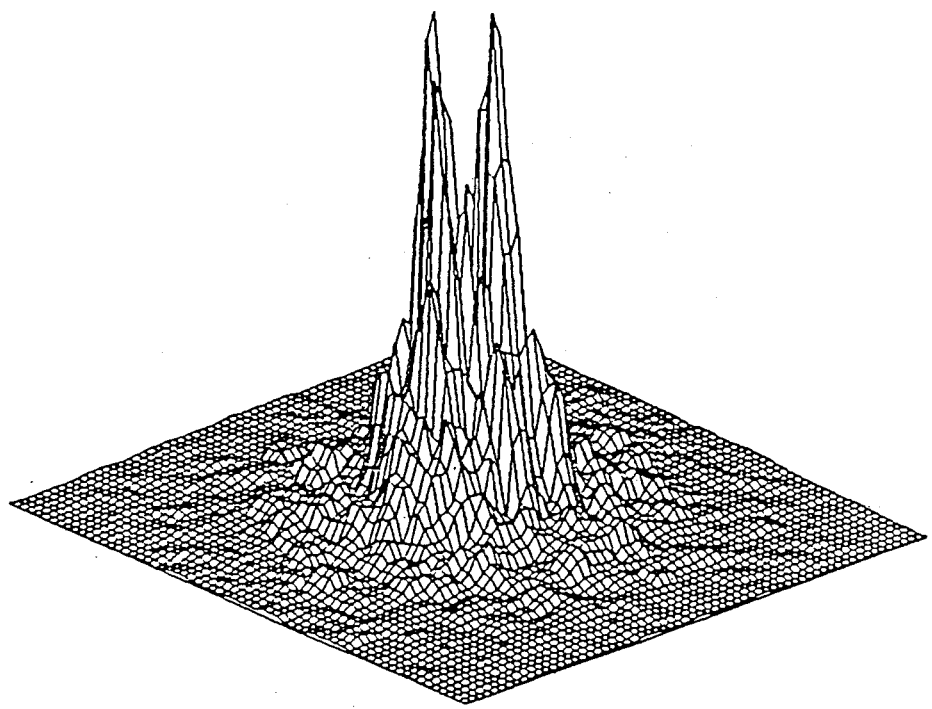
Figure 10A:
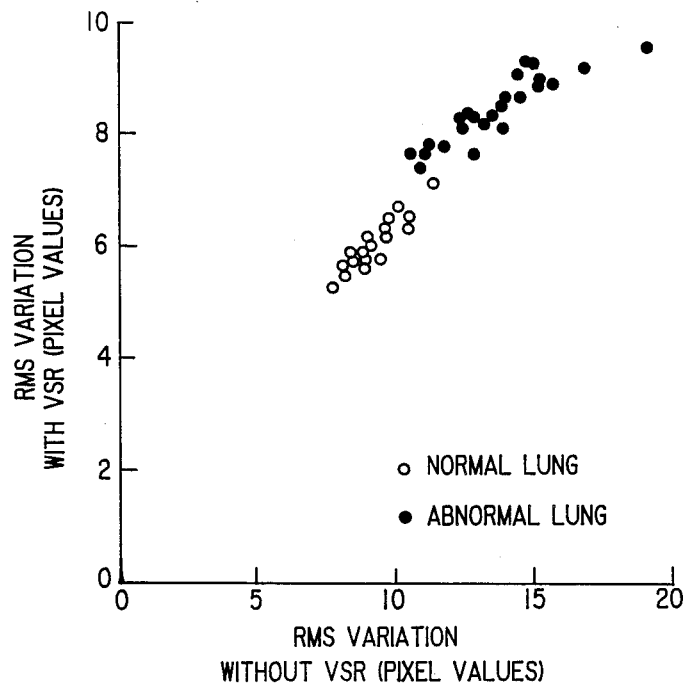
FIGS. 10a and 10b are graphs illustrating the effect of human visual response filtering on RMS variation and first moment of power spectrum, respectively, for normal and abnormal lungs.
Figure 10B:
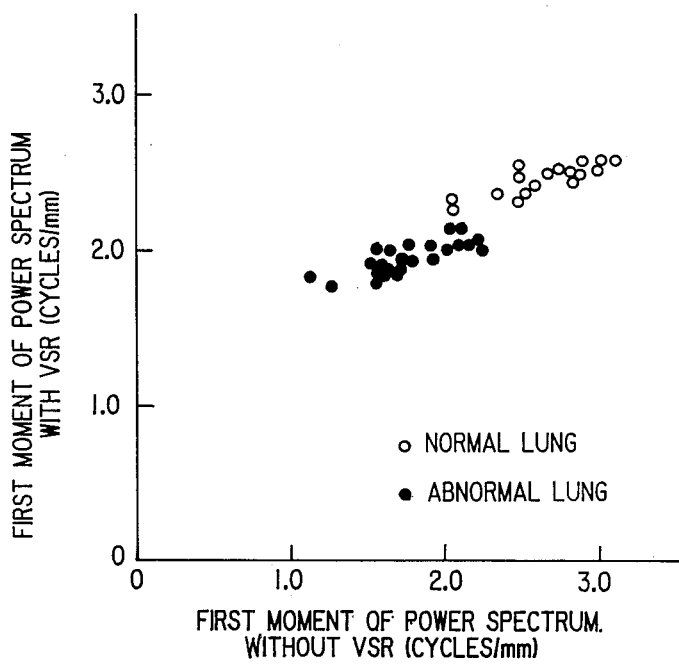

The power spectra of normal and abnormal lungs after the background trend correction has been applied are shown in FIGS. 9a and 9b, respectively. It is apparent that the power spectra of both lungs contain large low-frequency components, probably due to some residual "uncorrected" background trend. In addition, the power spectra include some components of very high frequencies due to radiographic mottle in the original chest radiograph (See Doi et al, HHS Publication FDA 82-8187, 1 (1982)). In order to suppress these unwanted components and to enhance the mid-frequency component related to "inherent" lung texture, the visual system response of human observers, which filters the power spectrum, is employed. Chan et al, (Proc. SPIE, 535, 2 (1985)) have derived an analytical function to approximate the visual system response of the human observer. This function is given by $$V(u,v) = \exp\left[\frac{(\ln\sqrt{u^2 + v^2} - \ln(25u_o/D))^2}{2(0.973)^2}\right], \quad (11)$$

where $u_o$ is the spatial frequency at which V(u) at a viewing distance, D, of 25 cm is a maximum. This is a useful expression since the visual system response can be shifted easily in the spatial frequency axis by a change in $u_o$ or D, which varies the peak position of the band pass filter. When $u_o$ was changed in the range from 0.5 to 4.0 cycles/mm, it was found that the difference in texture measures between the normal and abnormal lungs is largest when $u_o$ equals 1.5 cycles/mm. The filtered power spectra of the normal and abnormal lungs when the visual system response is used are shown in FIG. 9(c) and 9(d), where the scales of the filtered power spectra are expanded by a factor of eight for visual illustration. The rms variations and the first moments of the power spectra in various ROIs selected from the normal and abnormal lungs with and without human visual response filtering are shown in FIGS. 10(a) and 10(b), respectively. After filtering, the two texture measures of the normal lung are clearly distinguished from those of the abnormal lung.

Selection of Size and Location of Regions of Interest

Figure 11:
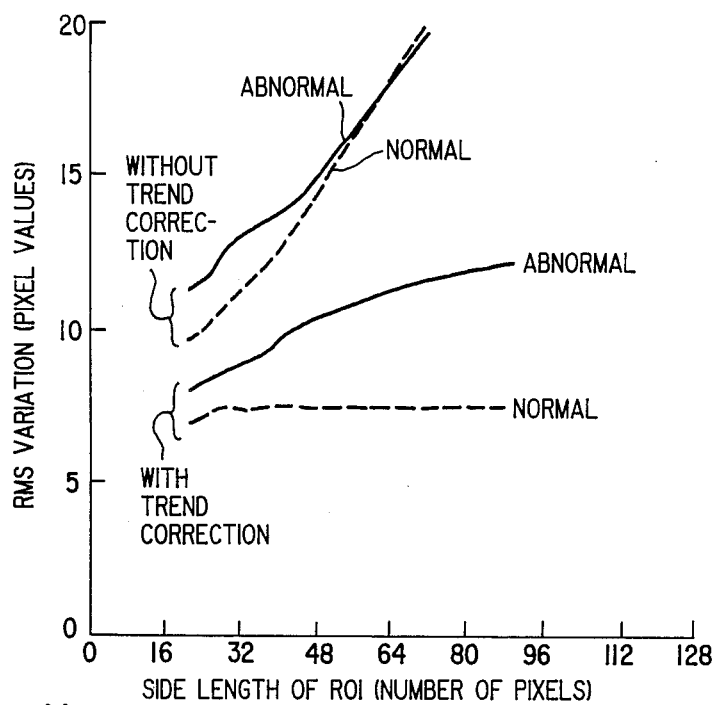
FIG. 11 is a graph illustrating the effect of ROI size on RMS variation for normal and abnormal lungs.

Since the lung textures need to be quantified with the exclusion of ribs and other obvious artifacts that may be part of a chest image, it is important to select an appropriate size as well as optimal locations for the ROIs in the inter-costal spaces. FIG. 11 shows the effect of varying the size of a square ROI on the rms variation for the normal lung and the abnormal lungs with a nodular pattern. Without the trend correction, the rms variation for both types of lungs increases rapidly as the ROI size increases. In addition, the rms variation for the abnormal lung is comparable to that of the normal lung for relatively large ROI sizes. After the trend correction, the rms variation of the normal lung becomes almost independent of the ROI size, whereas the rms variation of the abnormal lung increases gradually, thus increasing the difference between the two. This result may be related to the fact that a large ROI tends to give a better estimate of the statistical properties of lung texture; however, it also increased the possibility of error in the two-dimensional fitting of the overall background trend, thus yielding a misleadingly large rms variation. In order to reduce this error, one may need to employ a higher-order polynomial surface for fitting. A small ROI provides a reliable estimate of the background trend and is efficient for the computation of texture measures. In addition, since the fast-Fourier-transform (FFT) algorithm is used in calculating texture measures, it is efficient to use matrix sizes of the ROI with powers of two, such as 16, 32, 64, and 128. For all of these reasons, it was decided to employ a 64×64 pixel matrix (i.e., 6.4 mm×6.4 mm) for each ROI.

Figure 12:
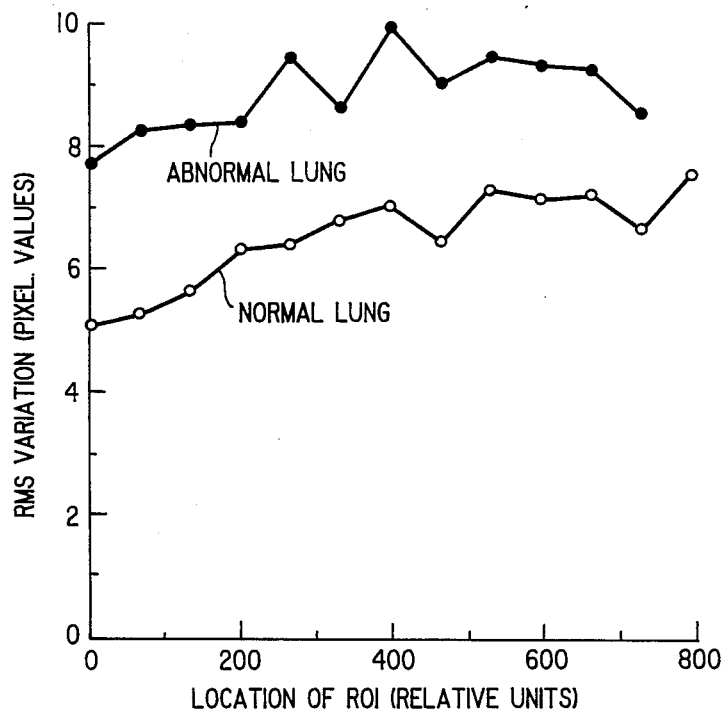
FIG. 12 is a graph illustrating the effect of ROI location on RMS variation, in which the relative locations of 0 and 800 are near the ribcage edge and in the hilar region, respectively.

The effect of the ROI location on the rms variation in the lung texture is shown in FIG. 12. The location of the ROI was varied from near the edge of the rib-cage to near the hilar region, which corresponds to 0 and 800 in terms of pixel location in the image matrix, respectively. Since there are large pulmonary vessels near the hilar region, the rms variation tends to increase gradually toward this area, as illustrated in both the normal and abnormal lungs. Because interstitial diseases tend to be more clearly visible in the peripheral lung regions, the analysis of lung texture is most accurate in these regions, where the overlap of large vessels is avoided. Therefore, two ROIs are selected in each inter-costal space at approximately 1/6 and 2/6 of the distance from the rib-cage edge to the center of the chest, as discussed above.

Removal of Artifacts

Small dust patterns and/or surface scratches are often present in conventional chest films. These unwanted artifacts may distort the calculated physical measures of lung texture. Though the number of these artifacts can be reduced if the chest radiograph is carefully selected, it is impossible to remove them completely. Therefore, it is necessary to eliminate the effect of these patterns on the measurement of actual lung texture. This is done according to the invention based on the finding that the histogram for the underlying fluctuating patterns of the lung texture has a virtually Gaussian distribution. Therefore, if a pixel value from the mean in the ROI is larger than four times the rms variation in the same ROI, the pixel value is assumed to be due to dust and/or scratches, and it is replaced by a pixel value that is sampled randomly from the Gaussian distribution having the same rms variation. With this method, the effect of dusts and/or scratches on texture measures appears to be completely corrected for.

Gridline in a chest radiograph can also pose a problem. Because gridlines are a periodic pattern, this artifact yields a large, sharp peak in the calculated power spectrum at the frequency that corresponds to the strip density of the grid, even though the contrast of these patterns is low. For removal of this effect, we suppress the peak due to the grid in the frequency domain by using an interpolation method. Since the stationary grids that are typically employed for chest examination include a strip density of 40 lines/cm, the maximum value of the power spectrum is searched in a corresponding square area (0.78 cycles/mm×0.78 cycles/mm) which was centered about the frequency (4 cycles/mm) that corresponded to the strip density. When the maximum value is significantly larger than the average value in the square area, the values of the power spectrum in a square area surrounding the large peak are replaced by estimated values using a bi-linear interpolation. With this correction technique, the effect of gridlines on texture measures can be reduced to a negligible level even when the gridlines are clearly visible.

Figure 13A:
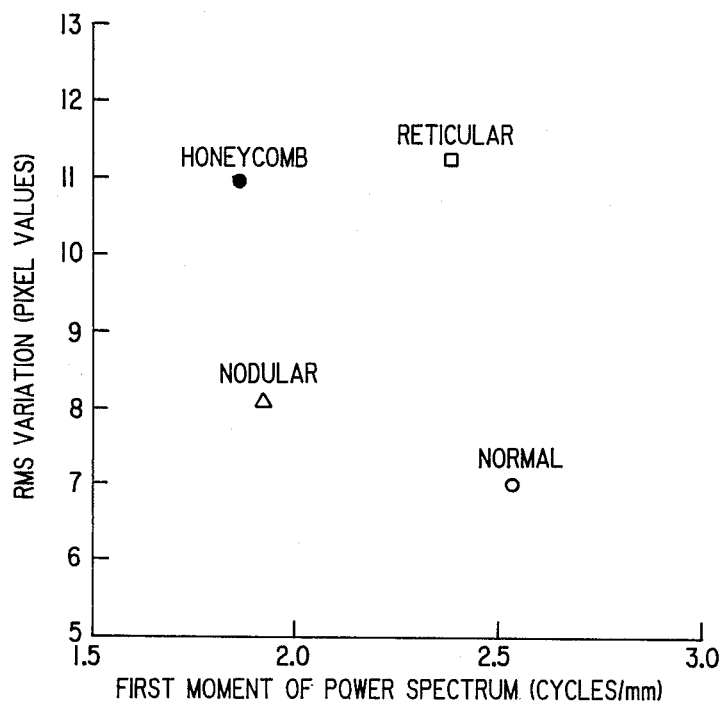
FIGS. 13a and 13b are graphs respectively illustrating texture measures of selected representative ROI's and texture measures from many ROI's for the four lungs, including one normal lung and three abnormal lungs with nodular, reticular, honeycomb patterns.

To evaluate the lung texture analysis technique of the invention, chest images of one normal and three abnormal lungs with nodular, reticular, and honeycomb patterns were obtained. Only one ROI for each chest image was selected for this comparison. The ROIs for the three abnormal lungs include relatively obvious representative patterns. The corresponding texture measures are shown in FIG. 13a. The nodular pattern has a low frequency content, and its rms variation is slightly larger than that of the normal lung; the reticular pattern has a large rms variation, and its frequency content is similar to that of the normal lung; and the honeycomb pattern has a large rms variation and a low frequency content. These results indicate clearly that these two texture measures can distinguish relatively obvious texture patterns in these abnormal lungs.

Figure 13B:
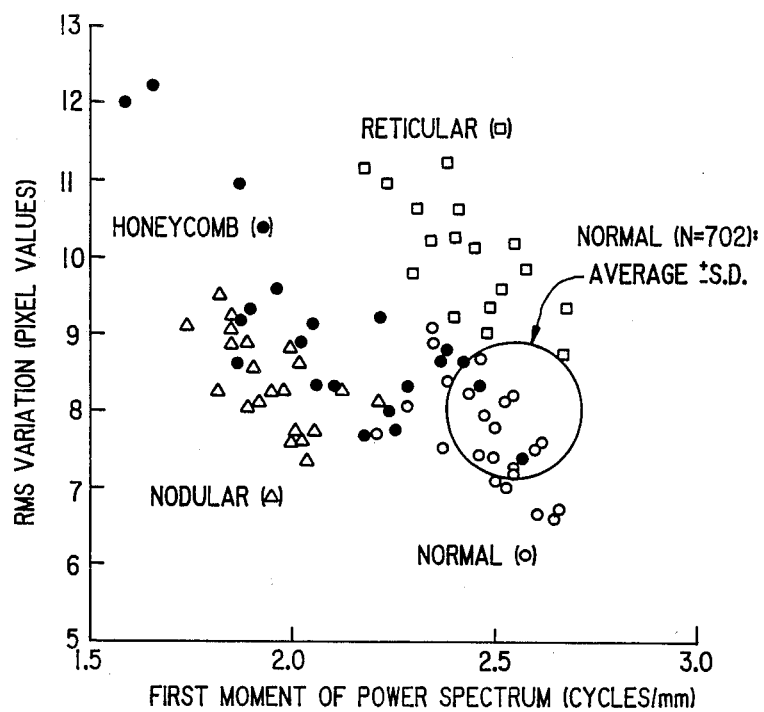

The texture measures from several ROIs selected in the four lungs are shown in FIG. 13b. The ellipse indicates the expected range (±one standard deviation) of texture measures for the average normal lung, estimated from 702 ROIs selected from 42 normal chest radiographs. The ellipse appears almost circular, since the scales of the two axes have been adjusted according to the standard deviations of the two texture measures. Texture measures for the abnormal lung with the honeycomb pattern are scattered widely, because the infiltrates are not uniformly distributed in this case; thus, the ROIs include both severely abnormal and minimally abnormal areas. Therefore, the variations of the two texture measures agree qualitatively with the patterns actually seen in the chest radiograph.

Figure 13C:
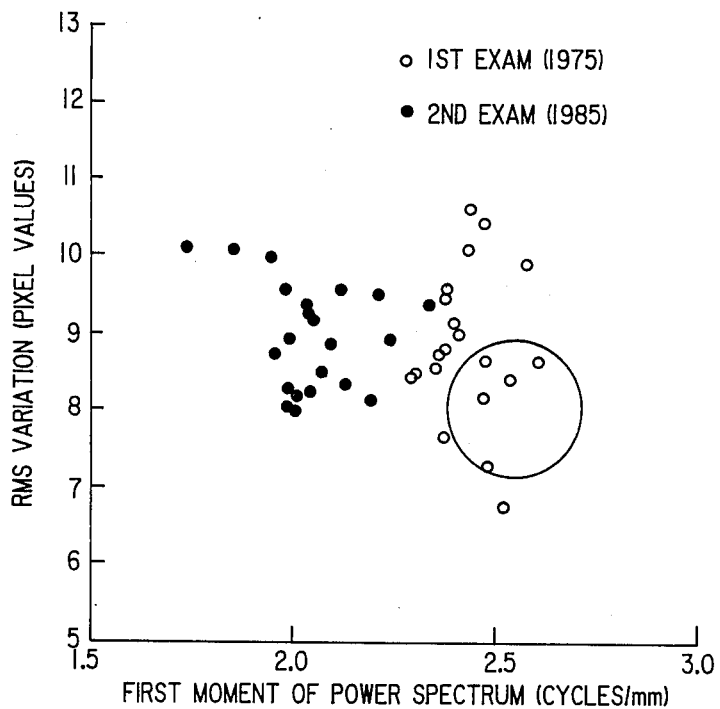
FIG. 13c is a graph illustrating the texture measures obtained from two chest images showing progressive interstitial infiltrate.

This analysis can be applied to the detection of changes in texture over time. Two chest images indicating a progressive interstitial infiltrate were obtained and their texture measures are plotted in FIG. 13c. The texture measures obtained from the chest image at the second examination are shifted toward low frequencies, indicating an increasingly nodular pattern. This result corresponds well to the radiographically observed progression.

As above discussed, the present invention provides a technique for the quantitation of lung textures in which the rms variation and the first moment of the power spectrum for digital chest radiographs are used in order to detect and characterize interstitial disease. Background trend correction is a crucially important step before the computation of the two texture measures, because it removes the effect of overall density variations and thus makes it possible to isolate the finely detailed pattern of the low-contrast lung texture due to interstitial disease from the overall gross lung anatomy in a chest radiograph. Filtering of the power spectrum by the human visual response is another important process with which one can selectively extract the mid-frequency components of the power spectrum; these components appear to be related most closely to interstitial disease. It is noted that the human visual response filtering employed according to the invention is a preferred form of bandpass filtering to suppress low frequency components due to residual uncorrected background trend and high frequency components due to radiographic mottle. However, other forms of bandpass filtering may also be useful depending on the hardware used in image acquisition.

Although it has been shown that background trend correction together with band-pass filtering improves the distinction of the rms variations between normal and abnormal lungs, one might argue that band-pass filtering alone could yield the same result, since suppression of low-frequency components by a filter is an edge enhancement operation and can be regarded as a form of background trend removal. However, this is not the case, as illustrated below.

Figure 14A:
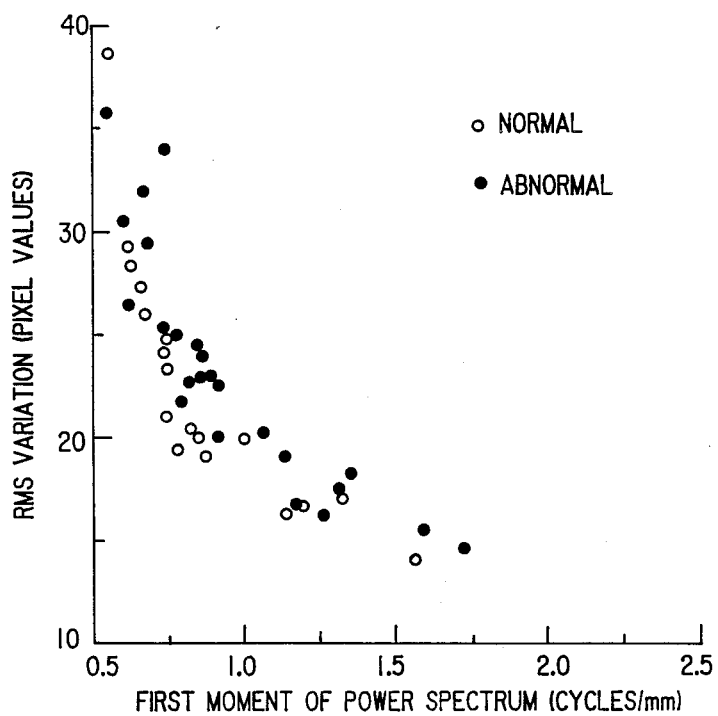
FIGS. 14a, 14b, 14c, and 14d are graphs illustrating texture measures for the normal and abnormal lungs (a) without trend correction and without filtering, (b) without trend correction but with filtering, (c) with trend correction but no filtering, and (d) with both trend correction and filtering, respectively.
Figure 14B:
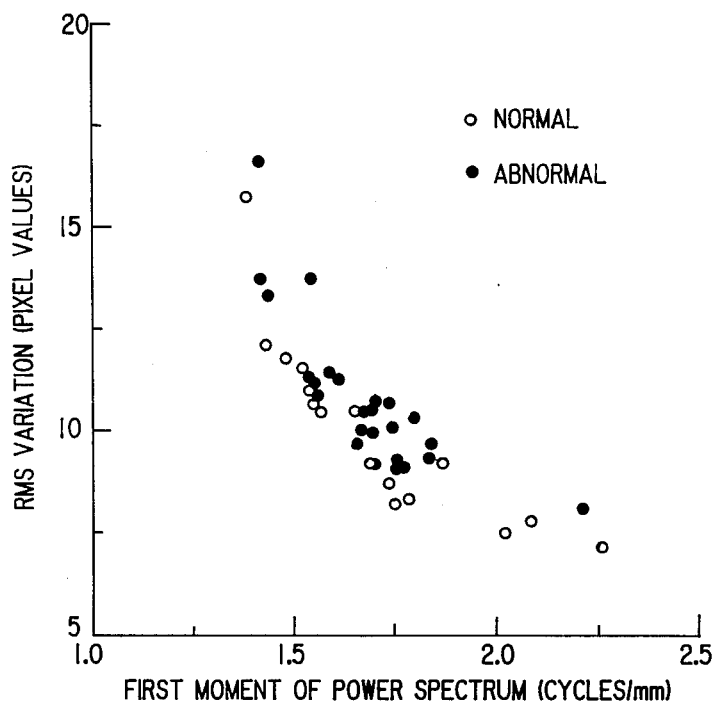
Figure 14C:
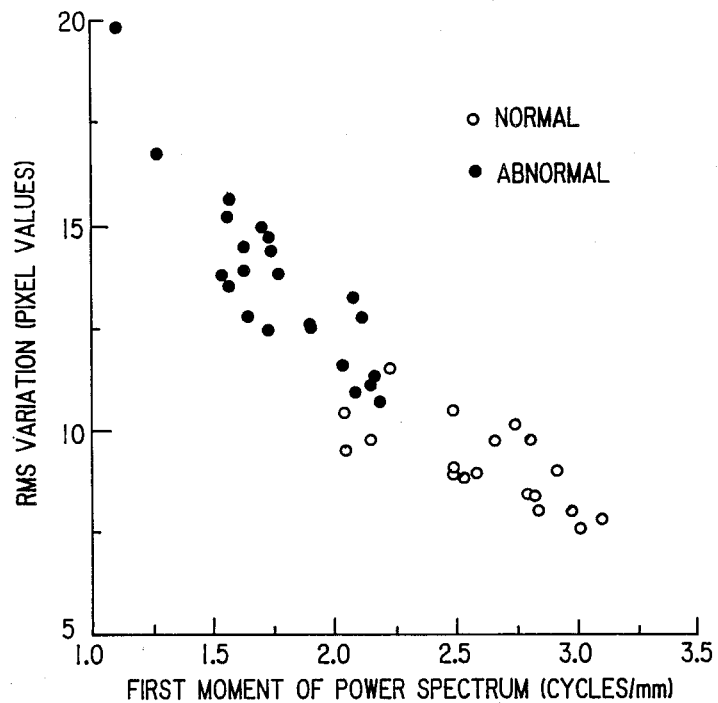
Figure 14D:
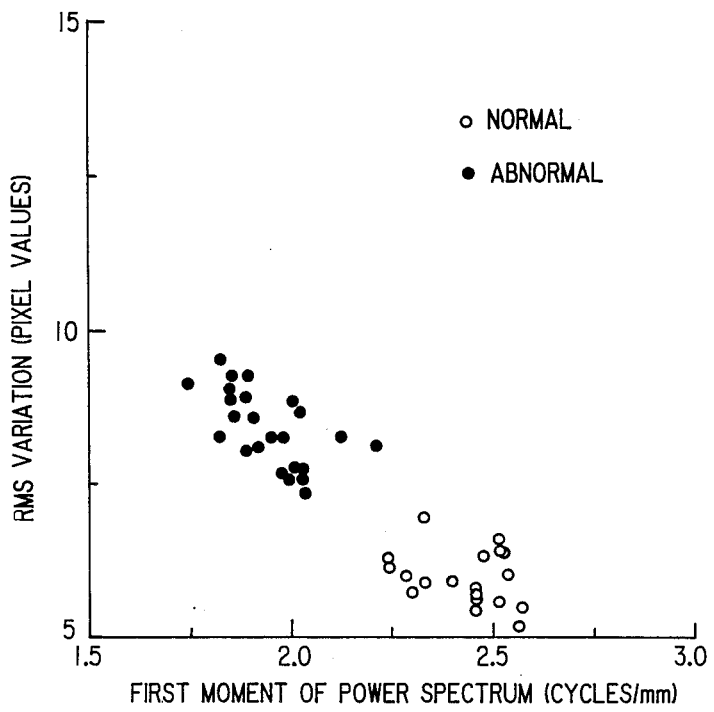

FIGS. 14a–14d show the texture measures of the normal and abnormal lungs obtained under four different pre-processing conditions. First, when neither trend correction nor filtering is performed, the texture measures of the normal lung are almost overlapped with those of the abnormal lung (FIG. 14a). Second, when only filtering by the visual system response is included, these texture measures largely overlap (FIG. 14b). Therefore, it appears that filtering by the visual system response alone cannot adequately correct the background for texture analysis. Third, when the background trend is corrected without filtering, the texture measures of the normal lung are almost completely separated from those of the abnormal lung (FIG. 14c). However, these measures for each lung are relatively widely distributed. Finally, when both the background trend correction and filtering are performed, the texture measures of the normal lung are separated completely from those of the abnormal lung, and each group of these measures is distributed in a relatively narrow area (FIG. 14d). Therefore, these results indicate that background trend correction by the second-order-polynomial curve fitting technique dramatically improves the separation of normal from abnormal lung textures, and that filtering by the human visual response further enhances the difference.

The two texture measures have been calculated in terms of pixel values, which are generally proportional to the optical density on the original radiograph, as described earlier. Therefore, the calculated texture measures are closely related to the pattern that radiologists perceive on the radiographs. However, if exposure factors such as the x-ray tube current and exposure time are varied, the corresponding optical densities on the radiograph will be altered while the texture of the lung remains the same. Therefore, it is desirable to employ texture measures that are independent of these variations. In fact, it is possible to obtain such measures if the optical density (or pixel value) is converted to the relative x-ray intensity incident on a detector system by employing the H&D curve of the screen-film system being used, (See Doi et al, HHS Publication FDA 82-8187:1 (1982) and Doi et al, HHS Publication FDA 86-8257:1 (1986)) employed for each chest radiograph. Such an individualized correction method may not be practical for the computation of texture measures in a large number of chest radiographs. However, if digital chest images are obtained with a fully automated digital system such as Fuji storage phosphor system, it will be possible to compute texture measures directly from the digital image data in terms of the relative x-ray intensity detected by a storage phosphor-laser readout system.

As above described, the present invention is also directed to a computerized technique of quantifying lung textures in terms of the rms variation and the first moment of the power spectrum of the lung pattern, which represents the magnitude and the coarseness (or fineness) of lung textures, respectively, in order to detect and characterize interstitial disease. As explained, it is necessary to isolate the patterns of the underlying lung textures by correcting for the non-uniform background trend. Moreover, filtering by the human visual response enhances the difference in texture measures between normal and the abnormal lungs. Using the technique of the invention, the rms variation and/or the first moment of the power spectrum for abnormal lungs with various interstitial diseases were found to be clearly different from those for normal lungs. These two texture measures, which are calculated from digital chest radiographs, are therefore useful to radiologists in their assessment of interstitial disease.

Figure 15:
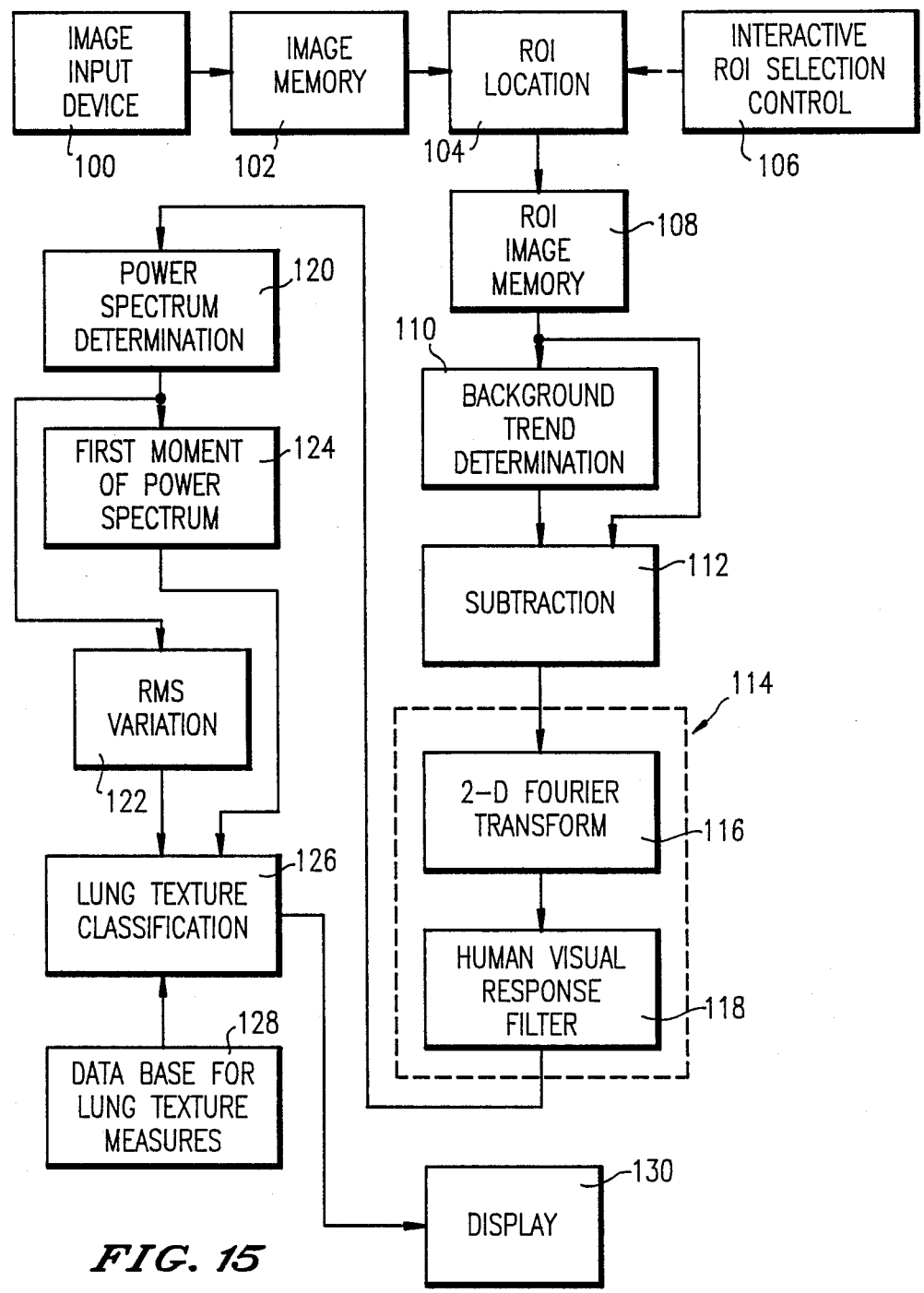
FIG. 15 is a schematic block diagram illustrating the method and system of automated lung texture analysis according to the present invention.

FIG. 15 is a schematic block diagram illustrating in sequential form the operation of a hard-wired automated system for analysis of lung texture. As shown in FIG. 15, image data corresponding to a radiographic chest image is first input (block 100) and stored in an image memory (block 102). In block 104, ROIs are located for subsequent texture analysis, as described above in connection with FIGS. 1a and 1b. In the event that manual assist of ROI location is desired, as above described in relation to FIG. 1b and particularly block 60, ROIs selected automatically are displayed and by means of conventional cursor control an operator can optionally assist in ROI location (block 106). Image data corresponding to selected ROIs are stored in memory (block 108) and for each stored ROI, the background trend is determined using a second-order polynomial two-dimensional (2-D) surface fit to the stored ROI image data (block 110). Thereafter, background trend is removed from the stored ROI image data using subtraction (block 112).

Once background trend is removed, the lung texture of the ROI is evaluated. First, the processed image data are subject to filtering (block 114) in which a 2-D Fourier transform is performed on the processed image data (block 116), with the result being then filtered by the human visual response (block 118), as above described. The power spectrum of the filtered image data is then determined (block 120) and from the power spectrum the RMS variation, R, is calculated (block 122). The filtered data are also in parallel processed to determine the first moment of the power spectrum of the filtered data, M, (block 124). Then, a lung texture classification is made of the ROI (block 126) based on predetermined criteria derived from a previously obtained database for lung texture measures (block 128), for example as shown in FIG. 13a or FIG. 14(d). The RMS variation R and the first moment of the power spectrum M are determined as follows:

$$R = \sqrt{\int_{-\infty}^{\infty} \int_{-\infty}^{\infty} V^2(u,v)\, T^2(u,v)\, du\, dv} \quad , \tag{12}$$

$$M = \frac{\int_{-\infty}^{\infty} \int_{-\infty}^{\infty} \sqrt{u^2 + v^2}\, V^2(u,v)\, T^2(u,v)\, du\, dv}{\int_{-\infty}^{\infty} \int_{-\infty}^{\infty} V^2(u,v)\, T^2(u,v)\, du\, dv} \tag{13}$$

where u and v are spatial frequencies in cartesian coordinates, and V(u,v) and T(u,v) correspond to the human visual response filter and the Fourier transform of the lung texture, respectively. The RMS variation R is expressed in terms of the pixel value, but it can also be described by other quantities. It should also be noted that the square of the Fourier transform of the lung texture, in an ROI is referred to as the power spectrum. Strictly speaking, however, the power spectrum needs to be determined from an ensemble average of the square of the Fourier transform over an infinitely large area. For example, referring to FIG. 14(d), if the processed ROI data has a first moment of power spectrum greater than 2.4 cycles/mm and an RMS variation less than 7.0 pixel values, the ROI is classified as "normal". If the processed ROI data on the other hand has a firs moment of power spectrum less than 2.4 cycles/mm and an RMS variation greater than 7.0 pixel values, the ROI is classified as abnormal. First moment of power spectrum data M and RMS variation data R for plural ROIs are displayed (block 128) to assist in ROI classification.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for automated analysis of lung texture in a radiographic chest image, comprising:

obtaining digital image data representative of said image;

selecting at least one region of interest (ROI) in said image for analysis;

removing background trend due to the gross anatomy of the lung and chest wall from the image data corresponding to said ROI and thereby producing corrected image data, representative of fluctuating patterns of the underlying lung texture, in which the background trend is removed;

processing the corrected image data to extract predetermined characteristics therefrom for evaluation.

2. The method according to claim 1, wherein said processing step comprises:
deriving objective texture measures based on the power spectrum of the corrected data.

3. The method according to claim 1, wherein said processing step comprises:
producing a two-dimensional (2D) Fourier transform of the corrected image data to obtain Fourier transformed data T(u,v), where u and v are spatial frequencies in a cartesian coordinate system;
bandpass filtering the Fourier transformed data T(u,v) to obtain filtered data;
determining the power spectrum of the filtered data; and
extracting at least one predetermined characteristic from the determined power spectrum.

4. The method according to claim 3, wherein said step of bandpass filtering comprises:
filtering T(u,v) by a human visual response, V(u,v), where $$V(u,v) = \exp\left[-\frac{(\ln\sqrt{u^2+v^2} - \ln(25\,u_0/D))^2}{2\,(0.973)^2}\right],$$

to obtain filtered data (T(u,v)V(u,v)), where $u_0$ and D are predetermined constants.

5. The method according to claim 4, wherein said extracting step comprises:
determining the root-mean-square (RMS) variation, R, of the power spectrum of the filtered data, where $$R = \sqrt{\int_{-\infty}^{\infty} V^2(u,v)\,T^2(u,v)\,du\,dv}\ .$$

6. The method according to claim 5, wherein said extracting step comprises:
determining the first moment of the power spectrum, M, of the filtered data, where $$M = \frac{\int_{-\infty}^{\infty}\int_{-\infty}^{\infty} \sqrt{u^2+v^2}\ V^2(u,v)\,T^2(u,v)\,du\,dv}{\int_{-\infty}^{\infty}\int_{-\infty}^{\infty} V^2(u,v)\,T^2(u,v)\,du\,dv}\ .$$

7. The method according to claim 6, wherein said background trend removing step comprises:
fitting a two-dimensional surface to the image data of said at least one ROI and obtaining two-dimensional fitting data corresponding to said surface; and
subtracting the two-dimensional fitting data from said ROI image data.

8. The method according to claim 7, wherein said ROI selecting step comprises:
boundary processing said digital image data to derive ribcage edge and midline boundaries;
deriving at least one vertical profile at predetermined locations in relation to the ribcage edge and midline boundaries derived in said boundary processing step;
removing background trend from the at least one vertical profile to obtain vertical profile corrected (VPC) data; and
selecting said at least one ROI based on said VPC data.

9. The method according to claim 8, wherein said boundary processing step comprises:
obtaining a horizontal signature at a horizontal line at a predetermined vertical location of said chest image from said image data;
determining a maximum value of said horizontal signature and defining the pixel location of that pixel having said maximum value as a midline boundary; and
determining a second derivative of said horizontal signature, detecting at which pixel said second derivative is a minimum, and defining the pixel location at which said second derivative is a minimum as an edge boundary.

10. The method according to claim 9, comprising:
obtaining edge boundaries from plural horizontal lines.

11. The method according to claim 10, wherein said vertical profile determining step comprises:
defining said at least one vertical profile based on pixel values of pixels located a predetermined distance from the edge boundaries determined during the repeated performance of said boundary processing step.

12. The method according to claim 11, wherein said step of selecting said at least one ROI comprises:
fitting a shift-variant sinusoidal function to said VPC data; and
selecting said at least one ROI based on the fitted shift-variant sinusoidal function.

13. The method according to claim 12, comprising:
displaying an image of said image data with the selected ROI superimposed thereon.

14. The method according to claim 13, comprising:
editing the at least one selected ROI by means of user interactive control of said displaying step.

15. The method according to claim 4, wherein said extracting step comprises:
determining the first moment of the power spectrum, M, of the filtered data, where $$M = \frac{\int_{-\infty}^{\infty}\int_{-\infty}^{\infty} \sqrt{u^2+v^2}\ V^2(u,v)\,T^2(u,v)\,du\,dv}{\int_{-\infty}^{\infty}\int_{-\infty}^{\infty} V^2(u,v)\,T^2(u,v)\,du\,dv}\ .$$

16. The method according to claim 1, wherein said background trend removing step comprises:
fitting a two-dimensional surface to the image data of said at least one ROI and obtaining two-dimensional fitting data corresponding to said surface; and
subtracting the two-dimensional fitting data from said ROI image data.

17. The method according to claim 16, wherein said fitting step comprises:

fitting a second-order polynomial surface to said image data.

18. The method according to claim 1, wherein said ROI selecting step comprises:
  boundary processing said digital image data to derive ribcage edge and midline boundaries;
  deriving at least one vertical profile at a predetermined locations in relation to the ribcage edge and midline boundaries derived in said boundary processing step;
  removing background trend from the at least one vertical profile to obtain vertical profile corrected (VPC) data; and
  selecting said at least one ROI based on said VPC data.

19. The method according to claim 18, wherein said boundary processing step comprises:
  obtaining a horizontal signature at a horizontal line at a predetermined vertical location of said chest image from said image data;
  determining a maximum value of said horizontal signature and defining the pixel location of that pixel having said maximum value as a midline boundary; and
  determining a second derivative of said horizontal signature, detecting at which pixel said second derivative is a minimum, and defining the pixel location at which said second derivative is a minimum as an edge boundary.

20. The method according to claim 19, comprising:
  obtaining edge boundaries from plural horizontal lines.

21. The method according to claim 20, wherein said vertical profile deriving step comprises:
  defining said at least one vertical profile based on pixel values of pixels located a predetermined distance from the edge boundaries determined during the repeated performance of said boundary processing step.

22. The method according to claim 21, wherein said step of selecting said at least one ROI comprises:
  fitting a shift-variant sinusoidal function to said VPC data; and
  selecting said at least one ROI based on the fitted shift-variant sinusoidal function.

23. The method according to claim 22, comprising:
  editing the at least one selected ROI by means of user interactive control of said displaying step.

24. The method according to claim 18, wherein said step of selecting said at least one ROI comprises:
  fitting a shift-variant sinusoidal function to said VPC data; and
  selecting said at least one ROI based on the fitted shift-variant sinusoidal function.

25. The method according to claim 24, comprising:
  displaying an image of said image data with the at least one selected ROI superimposed thereon.

26. A method for selecting at least one region of interest (ROI) for analysis of lung texture in a radiographic chest image, comprising:
  obtaining digital image data representative of said image;
  boundary processing said digital image data to derive ribcage edge and midline boundaries;
  deriving at least one vertical profile at a predetermined location in relation to the ribcage edge and midline boundaries derived in said boundary processing step;
  removing background trend from the at least one vertical profile to obtain vertical profile corrected (VPC) data;
  selecting said at least one ROI based on said VPC data.

27. The method according to claim 26, wherein said boundary processing step comprises:
  obtaining a horizontal signature at a horizontal line at a predetermined vertical location of said chest image from said image data;
  determining a maximum value of said horizontal signature and defining the pixel location of that pixel having said maximum value as a midline boundary; and
  determining a second derivative of said horizontal signature, detecting at which pixel said second derivative is a minimum, and defining the pixel location at which said second derivative is a minimum as an edge boundary.

28. The method according to claim 27, comprising:
  obtaining edge boundaries from plural horizontal lines.

29. The method according to claim 28, wherein said vertical profile determining step comprises
  defining said at least one vertical profile based on pixel values of pixel located at predetermined distance from the edge boundaries determined during the repeated performance of said boundary processing step.

30. The method according to claim 29, wherein said step of selecting said at least one ROI comprises:
  fitting a shift-variant sinusoidal function to said VPC data; and
  selecting said at least one ROI based on the fitted shift-variant sinusoidal function.

31. The method according to claim 26, wherein said step of selecting said at least one ROI comprises:
  fitting a shift-variant sinusoidal function to said VPC data; and
  selecting said at least one ROI based on the fitted shift-variant sinusoidal function.

32. The method according to claim 31, comprising:
  displaying an image of said image data with the selected ROI superimposed thereon.

33. The method according to claim 32, comprising:
  editing the at least one selected ROI by means of user interactive control of said displaying step.

34. A system for automated analysis of lung texture in a radiographic chest image, comprising:
  means for obtaining digital image data representative of said image;
  means for selecting at least one region of interest (ROI) in said image for analysis;
  means for removing background trend due to the gross anatomy of the lung and chest wall from the image data corresponding to said ROI and thereby producing corrected image data, representative of fluctuating patterns of the underlying lung texture, in which the background trend is removed;
  processing means for extracting from the corrected image data predetermined characteristics for evaluation.

35. The system according to claim 34, wherein said processing means comprises:
  means for producing a two-dimensional (2D) Fourier transform of the corrected image data to obtain Fourier transformed data $T(u,v)$;
  means for bandpass filtering $T(u,v)$;

means for determining the power spectrum of the filtered data;

means for determining the root-mean-square (RMS) variation, R, of the power spectrum of the Fourier transformed data, where $$R = \sqrt{\int_{-\infty}^{\infty} V^2(u,v) \, T^2(u,v) du dv} \; ; \text{ and}$$

means for determining the first moment of the power spectrum, M, of the Fourier transformed data, where $$M = \frac{\int_{-\infty}^{\infty} \int_{-\infty}^{\infty} \sqrt{u^2 + v^2} \, V^2(u,v) \, T^2(u,v) du dv}{\int_{-\infty}^{\infty} \int_{-\infty}^{\infty} V^2(u,v) \, T^2(u,v) du dv} \; ;$$

where V(u,v) defines the filter characteristic of said bandpass filtering means, and u and v are spatial frequencies in cartesian coordinates.

36. The system according to claim 35, wherein the characteristic V(u,v) of said bandpass filtering means is defined in terms of the human visual response as follows:

$$V(u,v) = \exp\left[ - \frac{(\ln\sqrt{u^2 + v^2} - \ln(25 \, u_o/D))^2}{2\,(0.973)^2} \right],$$

where $u_o$ and D are predetermined constants.

37. The system according to claim 36, wherein said background trend removing means comprises:
  means for fitting a two-dimensional surface to the image data of said at least one ROI and obtaining two-dimensional fitting data corresponding to said surface; and
  means for subtracting the two-dimensional fitting data from said ROI image data.

38. The system according to claim 37, wherein said ROI selecting step comprises:
  boundary processing means for determining from said digital image data ribcage edge and midline boundaries;
  means for deriving at least one vertical profile at predetermined locations in relation to the ribcage edge and midline boundaries determined by said processing means;
  removing background trend from the at least one vertical profile to obtain vertical profile corrected (VPC) data; and
  means for selecting said at least one ROI based on said VPC data.

39. The system according to claim 38, wherein said boundary processing means comprises
  means for a horizontal signature at a horizontal line at a predetermined vertical location of said chest image from said image data;
  means for determining a maximum value of said horizontal signature, wherein the pixel location of that pixel having said maximum value is defined as a midline boundary; and
  means for determining a second derivative of said horizontal signature and detecting at which pixel said second derivative is a minimum, wherein the pixel location at which said second derivative is a minimum is defined as an edge boundary.

40. The system according to claim 39, comprising:
  means for obtaining edge and midline boundaries for plural horizontal lines.

41. The system according to claim 40, wherein said vertical profile deriving means comprises:
  means for determining said at least one vertical profile based on pixel values of pixels located a predetermined distance from the edge boundaries determined for said plural horizontal lines.

42. The system according to claim 41, wherein said means for selecting said at least one ROI comprises:
  means for fitting a shift-variant sinusoidal function to said VPC data; and
  means for selecting said at least one ROI based on the fitted shift-variant sinusoidal function.

43. The system according to claim 42, comprising:
  means for displaying an image of said image data with the selected ROI superimposed thereon.

44. The method according to claim 43, comprising:
  user interactive control means for editing the at least one selected ROI.

45. The system according to claim 34, wherein said background trend removing means comprises:
  means for fitting a two-dimensional surface to the image data of said at least one ROI and obtaining two-dimensional fitting data corresponding to said surface; and
  means for subtracting the two-dimensional fitting data from said ROI image data.

46. The system according to claim 45, wherein said fitting means comprises:
  means for fitting a second-order polynomial surface to said image data.

47. The system according to claim 34, wherein said ROI selecting means comprises:
  boundary processing means for determining from said digital image data ribcage edge and midline boundaries;
  means for deriving at least one vertical profile at a predetermined location in relation to the ribcage edge and midline boundaries determined by said boundary processing means;
  means for removing background trend from the at least one vertical profile to obtain vertical profile corrected (VPC) data; and
  means for selecting said at least one ROI based on said VPC data.

48. The method according to claim 47, wherein said boundary processing means comprises
  means for obtaining a horizontal signature at a horizontal line at a predetermined vertical location of said chest image from said image data;
  means for determining a maximum value of said horizontal signature wherein the pixel location of that pixel having said maximum value is defined as a midline boundary; and
  means for determining a second derivative of said horizontal signature and detecting at which pixel said second derivative is a minimum, wherein the pixel location at which said second derivative is a minimum is defined as an edge boundary.

49. The system according to claim 48, wherein said boundary processing means comprises:
  means for obtaining edge and midline boundaries for plural horizontal lines.

50. The system according to claim 49, wherein said vertical profile deriving means comprises:
 means for determining said at least one vertical profile based on pixel values of pixels located a predetermined distance from the edge boundaries determined for said plural horizontal signatures.

51. The system according to claim 50, wherein said means for selecting said at least one ROI comprises:
 means for fitting a shift-variant sinusoidal function to said VPC data; and
 means for selecting said at least one ROI based on the fitted shift-variant sinusoidal function.

52. The system according to claim 47, wherein said means for selecting said at least one ROI comprises:
 means for fitting a shift-variant sinusoidal function to said VPC data; and
 means for selecting said at least one ROI based on the fitted shift-variant sinusoidal function.

53. The system according to claim 52, comprising:
 means for displaying an image of said image data with the at least one selected ROI superimposed thereon.

54. The system according to claim 53, comprising:
 interactive control means for editing the at least one selected ROI.

55. A system for selecting at least one region of interest (ROI) for analysis of lung texture in a radiographic chest image, comprising:
 means for obtaining digital image data representative of said image;
 boundary processing means for deriving from said digital image data ribcage edge and midline boundaries;
 means for deriving at least one vertical profile at a predetermined location in relation to the ribcage edge and midline boundaries derived by said boundary processing means;
 means for removing background trend from the at least one vertical profile to obtain vertical profile corrected (VPC) data; and
 means for selecting said at least one ROI based on said VPC data.

56. The system according to claim 55, wherein said boundary processing means comprises:
 means for obtaining a horizontal signature at a predetermined vertical location of said chest image from said image data;
 means for determining a maximum value of said horizontal signature, wherein the pixel location of that pixel having said maximum value is defined as a midline boundary; and
 means for determining a second derivative of said horizontal signature and detecting at which pixel said second derivative is a minimum, wherein the pixel location at which said second derivative is a minimum is defined as an edge boundary.

57. The system according to claim 56, comprising:
 means for obtaining edge and midline boundaries for plural horizontal lines.

58. The system according to claim 57, wherein said vertical profile determining means comprises:
 means for determining said at least one vertical profile based on pixel values of pixels located a predetermined distance from the edge boundaries determined for said plural horizontal lines.

59. The system according to claim 58, wherein said step of selecting said at least one ROI comprises:
 means for fitting a shift-variant sinusoidal function to said VPC data; and
 means for selecting said at least one ROI based on the fitted shift-variant sinusoidal function.

60. The system according to claim 55, wherein said step of selecting said at least one ROI comprises:
 means for fitting a shift-variant sinusoidal function to said VPC data; and
 means for selecting said at least one ROI based on the fitted shift-variant sinusoidal function.

61. The system according to claim 60, comprising:
 means for displaying an image of said image data with the selected ROI superimposed thereon.

62. The system according to claim 61, comprising:
 interactive control means for editing the at least one selected ROI.

* * * * *

UNITED STATES PATENT AND TRADEMARK OFFICE
CERTIFICATE OF CORRECTION

PATENT NO. :   4,851,984

DATED      :   July 25, 1989

INVENTOR(S) :  KUNIO DOI, ET AL

It is certified that error appears in the above-identified patent and that said Letters Patent is hereby corrected as shown below:

In Column 1, line 5, before "BACKGROUND OF THE INVENTION" insert the following paragraph:

The present invention was made in part with U.S. Government support under grant number 2 R01 CA24806-11 from the Department of Health and Human Services and National Cancer Institute. The U.S. Government has certain rights in the invention.

Signed and Sealed this

Twenty-first Day of April, 1992

Attest:

HARRY F. MANBECK, JR.

*Attesting Officer*　　　　*Commissioner of Patents and Trademarks*